(12) United States Patent
Gryaznov et al.

(10) Patent No.: US 7,989,603 B2
(45) Date of Patent: Aug. 2, 2011

(54) 2'-ARABINO-FLUOROOLIGONUCLEOTIDE N3'-P5' PHOSPHORAMIDATES: THEIR SYNTHESIS AND USE

(75) Inventors: Sergei Gryaznov, San Mateo, CA (US); Ronald G. Schultz, Urbana, MO (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 12/004,123

(22) Filed: Dec. 20, 2007

(65) Prior Publication Data
US 2008/0171859 A1    Jul. 17, 2008

Related U.S. Application Data

(62) Division of application No. 10/181,823, filed as application No. PCT/US01/01918 on Jan. 19, 2001, now Pat. No. 7,321,029.

(60) Provisional application No. 60/178,248, filed on Jan. 21, 2000.

(51) Int. Cl.
| | |
|---|---|
| C07H 19/00 | (2006.01) |
| C07H 19/06 | (2006.01) |
| C07H 19/09 | (2006.01) |
| C07H 19/16 | (2006.01) |
| C07H 19/19 | (2006.01) |

(52) U.S. Cl. ............... 536/22.1; 536/26.1; 536/28.1; 536/28.4; 536/27.81; 536/27.6; 514/42

(58) Field of Classification Search ............ 536/22.1, 536/26.1, 28.1, 28.4, 27.81, 27.6; 514/42
See application file for complete search history.

(56) References Cited

U.S. PATENT DOCUMENTS 5,684,143 A    11/1997    Gryaznov et al.

FOREIGN PATENT DOCUMENTS

| JP | 01104092 A | * | 4/1989 |
|---|---|---|---|
| WO | WO 91/10671 | | 7/1991 |

OTHER PUBLICATIONS

STN Abstract of Morisawa et al., JP 0-1104092 A, Apr. 21, 1989.*
Morisawa et al..; JP 01104092 A, Apr. 21, 1989, English Translation.*
Gryaznov et al., *Nucleic Acids Res.*, 24(8):1508-1514 (1996).
Ikeda et al., *Nucleic Acids Res.*, 26(9):2237-2244 (1998).
Kawasaki et al., *J. Med. Chem.*, 36:831-841 (1993).
Schultz and Gryaznov, *Nucleic Acids Res.*, 24(15):2966-2973 (1996).
Skorski et al., *PNAS*, 94:3966-3971 (1997).
International Search Report for PCT/US01/01918, Geron Corporation, May 29, 2001.
Schultz, R. and Gryaznov, S., *Tetrahedron Letters*, 41:1895-1899 (2000).

* cited by examiner

*Primary Examiner* — Shaojia Anna Jiang
*Assistant Examiner* — Michael C Henry
(74) *Attorney, Agent, or Firm* — Leslie A. Mooi

(57) ABSTRACT

Oligonucleotides with a novel sugar-phosphate backbone containing at least one 2'-arabino-fluoronucleoside and an internucleoside 3'-NH—P(=O)(OR)—O-5' linkage, where R is a positively charged counter ion or hydrogen, and methods of synthesizing and using the inventive oligonucleotides are provided. The inventive phosphoramidate 2'-arabino-fluorooligonucleotides have a high RNA binding affinity to complementary nucleic acids and are base and acid stable.

5 Claims, 3 Drawing Sheets

SEQUENCE LISTING

```
<160> NUMBER OF SEQ ID NOS: 23

<210> SEQ ID NO 1
<211> LENGTH: 3
<212> TYPE: DNA
<213> ORGANISM: Artificial Sequence
<220> FEATURE:
<223> OTHER INFORMATION: contains 2 prime-deoxy and 2 prime-arabino-
      fluoronucleosides
```

-continued

```
<220> FEATURE:
<221> NAME/KEY: misc_feature
<223> OTHER INFORMATION: model trinucleoside

<400> SEQUENCE: 1 tuu                                                                        3

<210> SEQ ID NO 2
<211> LENGTH: 2
<212> TYPE: DNA
<213> ORGANISM: Artificial Sequence
<220> FEATURE:
<223> OTHER INFORMATION: contains 2 prime-deoxy and 2 prime-arabino-
      fluoronucleosides
<220> FEATURE:
<221> NAME/KEY: misc_feature
<223> OTHER INFORMATION: model dinucleoside

<400> SEQUENCE: 2 ut                                                                         2

<210> SEQ ID NO 3
<211> LENGTH: 10
<212> TYPE: DNA
<213> ORGANISM: Artificial Sequence
<220> FEATURE:
<223> OTHER INFORMATION: contains 2 prime-deoxy nucleosides
<220> FEATURE:
<221> NAME/KEY: misc_feature
<223> OTHER INFORMATION: test compounds

<400> SEQUENCE: 3
uuuuuuuuut                                                                10

<210> SEQ ID NO 4
<211> LENGTH: 10
<212> TYPE: DNA
<213> ORGANISM: Artificial Sequence
<220> FEATURE:
<223> OTHER INFORMATION: contains 2 prime-ribo-fluoronucleosides
<220> FEATURE:
<221> NAME/KEY: misc_feature
<223> OTHER INFORMATION: test compounds

<400> SEQUENCE: 4
uuuuuuuuut                                                                10

<210> SEQ ID NO 5
<211> LENGTH: 10
<212> TYPE: DNA
<213> ORGANISM: Artificial Sequence
<220> FEATURE:
<223> OTHER INFORMATION: contains 2 prime-arabino-nucleosides
<220> FEATURE:
<221> NAME/KEY: misc_feature
<223> OTHER INFORMATION: test compounds

<400> SEQUENCE: 5
uuuuuuuuut                                                                10

<210> SEQ ID NO 6
<211> LENGTH: 10
<212> TYPE: DNA
<213> ORGANISM: Artificial Sequence
<220> FEATURE:
<223> OTHER INFORMATION: contains 2 prime-deoxy nucleosides
<220> FEATURE:
<221> NAME/KEY: misc_feature
<223> OTHER INFORMATION: test compounds
```

-continued

```
<400> SEQUENCE: 6
uuuuuuuuut                                                                 10

<210> SEQ ID NO 7
<211> LENGTH: 10
<212> TYPE: DNA
<213> ORGANISM: Artificial Sequence
<220> FEATURE:
<223> OTHER INFORMATION: contains 2 prime-deoxy and 2 prime-ribo-
      fluoronucleotides
<220> FEATURE:
<221> NAME/KEY: misc_feature
<223> OTHER INFORMATION: test compounds

<400> SEQUENCE: 7
tuuuuuuuuu                                                                 10

<210> SEQ ID NO 8
<211> LENGTH: 10
<212> TYPE: DNA
<213> ORGANISM: Artificial Sequence
<220> FEATURE:
<223> OTHER INFORMATION: contains 2 prime-deoxy and 2 prime-arabino-
      fluoronucleosides
<220> FEATURE:
<221> NAME/KEY: misc_feature
<223> OTHER INFORMATION: test compounds

<400> SEQUENCE: 8
tuuuuuuuuu                                                                 10

<210> SEQ ID NO 9
<211> LENGTH: 9
<212> TYPE: DNA
<213> ORGANISM: Artificial Sequence
<220> FEATURE:
<223> OTHER INFORMATION: contains 2 prime-deoxy nucleosides
<220> FEATURE:
<221> NAME/KEY: misc_feature
<223> OTHER INFORMATION: test compounds

<400> SEQUENCE: 9 cucucugcc                                                                   9

<210> SEQ ID NO 10
<211> LENGTH: 9
<212> TYPE: DNA
<213> ORGANISM: Artificial Sequence
<220> FEATURE:
<223> OTHER INFORMATION: contains 2 prime-arabino-fluoronucleosides
<220> FEATURE:
<221> NAME/KEY: misc_feature
<223> OTHER INFORMATION: test compounds

<400> SEQUENCE: 10 cucucugcc                                                                   9

<210> SEQ ID NO 11
<211> LENGTH: 28
<212> TYPE: DNA
<213> ORGANISM: Homo sapiens

<400> SEQUENCE: 11
tgtgtggtag acctgttacc agagggag                                             28

<210> SEQ ID NO 12
<211> LENGTH: 26
<212> TYPE: DNA
```

<213> ORGANISM: Homo sapiens

<400> SEQUENCE: 12
ctaaccctaa ctggtaacag gtctac                                              26

<210> SEQ ID NO 13
<211> LENGTH: 6
<212> TYPE: DNA
<213> ORGANISM: Homo sapiens

<400> SEQUENCE: 13 ttaggg                                                                     6

<210> SEQ ID NO 14
<211> LENGTH: 18
<212> TYPE: DNA
<213> ORGANISM: Homo sapiens

<400> SEQUENCE: 14
aatccgtcga gcagagtt                                                       18

<210> SEQ ID NO 15
<211> LENGTH: 21
<212> TYPE: DNA
<213> ORGANISM: Homo sapiens

<400> SEQUENCE: 15
ccctaaccct aaccctaacc c                                                   21

<210> SEQ ID NO 16
<211> LENGTH: 11
<212> TYPE: DNA
<213> ORGANISM: Homo sapiens

<400> SEQUENCE: 16
gttagggtta g                                                              11

<210> SEQ ID NO 17
<211> LENGTH: 11
<212> TYPE: DNA
<213> ORGANISM: Homo sapiens

<400> SEQUENCE: 17
gttgagtgta g                                                              11

<210> SEQ ID NO 18
<211> LENGTH: 13
<212> TYPE: DNA
<213> ORGANISM: Homo sapiens

<400> SEQUENCE: 18
tagggttaga caa                                                            13

<210> SEQ ID NO 19
<211> LENGTH: 13
<212> TYPE: DNA
<213> ORGANISM: Homo sapiens

<400> SEQUENCE: 19
taggtgtaag caa                                                            13

<210> SEQ ID NO 20
<211> LENGTH: 11
<212> TYPE: DNA

```
-continued

<213> ORGANISM: Homo sapiens

<400> SEQUENCE: 20
gttagggtta g                                                       11

<210> SEQ ID NO 21
<211> LENGTH: 11
<212> TYPE: DNA
<213> ORGANISM: Homo sapiens

<400> SEQUENCE: 21
gttgagtgta g                                                       11

<210> SEQ ID NO 22
<211> LENGTH: 13
<212> TYPE: DNA
<213> ORGANISM: Homo sapiens

<400> SEQUENCE: 22
tagggttaga caa                                                     13

<210> SEQ ID NO 23
<211> LENGTH: 13
<212> TYPE: DNA
<213> ORGANISM: Homo sapiens

<400> SEQUENCE: 23
taggtgtaag caa                                                     13
```

2'-ARABINO-FLUOROOLIGONUCLEOTIDE N3'→P5' PHOSPHORAMIDATES: THEIR SYNTHESIS AND USE

CROSS-REFERENCE TO RELATED APPLICATIONS

This application is a divisional of U.S. patent application Ser. No. 10/181,823 filed May 29, 2003 now U.S. Pat. No. 7,321,029, which is a national stage application of International Application. No. PCT/US01/01918 filed on Jan. 19, 2001, which claims priority from U.S. Application No. 60/178,248, filed Jan. 21, 2000, all of which are hereby incorporated herein by reference in their entirety.

FIELD OF THE INVENTION

The present invention relates to 2'-arabino-fluorooligonucleotide N3'→P5' phosphoramidates. More particularly, the invention is directed to 2'-arabino-fluoro monomer and oligonucleotide phosphoramidate compositions, their use as diagnostic or therapeutic agents and methods for synthesizing phosphoramidate oligonucleotides containing said 2'-arabino-fluorooligonucleotides.

BACKGROUND OF THE INVENTION

Nucleic acid polymer chemistry has played a crucial role in many developing technologies in the pharmaceutical, diagnostic, and analytical fields, and more particularly in the subfields of antisense and anti-gene therapeutics, combinatorial chemistry, branched DNA signal amplification, and array-based DNA diagnostics and analysis (e.g., Uhlmann and Peyman, *Chemical Reviews*, 90:543-584, 1990; Milligan et al., *J. Med. Chem.* 36:1923-1937, 1993; DeMesmaeker et al., *Current Opinion in Structural Biology*, 5:343-355, 1995; Roush, *Science*, 276:1192-1193, 1997; Thuong et al., *Angew. Chem. Int. Ed. Engl.*, 32:666-690, 1993; Brenner et al., *Proc. Natl. Acad. Sci.*, 89:5381-5383, 1992; Gold et al., *Ann. Rev. Biochem.*, 64.763-797, 1995; Gallop et al., *J. Med. Chem.*, 37:1233-1258, 1994; Gordon et al., *J. Med. Chem.*, 37:1385-1401, 1994; Gryaznov, International application No. PCT/US94/07557; Urdea et al., U.S. Pat. No. 5,124,246; Southern et al., *Genomics*, 13:1008-1017, 1992; McGall et al., U.S. Pat. No. 5,412,087; Fodor et al., U.S. Pat. No. 5,424,186; Pirrung et al., U.S. Pat. No. 5,405,783).

Much of this chemistry has been directed to improving the binding strength, specificity, and nuclease resistance of natural nucleic acid polymers, such as DNA. Unfortunately, improvements in one property, such as nuclease resistance, often involve trade-offs against other properties, such as binding strength. Examples of such trade-offs abound: peptide nucleic acids (PNAs) display good nuclease resistance and binding strength, but have reduced cellular uptake in test cultures (e.g., Hanvey et al., *Science*, 258:1481-1485, 1992); phosphorothioates display good nuclease resistance and solubility, but are typically synthesized as P-chiral mixtures and display several sequence-non-specific biological effects (e.g., Stein et al., *Science*, 261:1004-1012, 1993); methylphosphonates display good nuclease resistance and cellular uptake, but are also typically synthesized as P-chiral mixtures and have reduce duplex stability (e.g., DeMesmaeker et al. (cited above); and so on.

Recently, a new class of oligonucleotide analog has been developed having so-called N3'→P5' phosphoramidate internucleoside linkages which display favorable binding properties, nuclease resistance, and solubility (Gryaznov and Letsinger, *Nucleic Acids Research*, 20:3403-3409, 1992; Chen et al., *Nucleic Acids Research*, 23:2661-2668, 1995; Gryaznov et al., *Proc. Natl. Acad. Sci.*, 92:5798-5802, 1995; and Gryaznov et al., *J. Am. Chem. Soc.*, 116:3143-3144, 1994). Phosphoramidate compounds contain a 3'-amino group at each of the 2'-deoxyfuranose nucleoside residues replacing a 3'-oxygen atom. The synthesis and properties of oligonucleotide N3'→P5' phosphoramidates are also described in Gryaznov et al., U.S. Pat. Nos. 5,591,607; 5,599,922; 5,726,297; and Hirschbein et al., U.S. Pat. No. 5,824,793.

Oligonucleotides with various modifications of the internucleoside linkages and 2'-position of the sugar rings have been described. Among these compounds are phosphodiester (PO), and phosphorothioate (PS) oligonucleotides containing 2'-fluoro substituents in ribo- or in arabino-configurations (Kawasaki et al., *J. Med. Chem.* 36:831-841, 1993; Ikeda et al., *Nucl. Acids Res.*, 26:2217-2244, 1998; Kois et al., *Nucleosides Nucleotides*, 12:1093-1109, 1993). Of these the oligo-2'-ribo-fluoronucleotides form the most stable complexes with DNA and RNA, whereas stability of duplexes formed by the isomeric oligo-2'-arabino-fluoro nucleotides is significantly lower. The duplex stabilizing effects of 2'-ribo-fluoronucleotides was mainly attributed to their C3'-endo or N-type sugar puckering (Kawasaki et al., *J. Med. Chem.* 36:831-841, 1993). Unfortunately, phosphodiester oligo-2'-ribo-fluoronucleotides are not resistant to hydrolysis by cellular nucleases, and require further modification of the internucleoside linking groups for any in vivo applications of these compounds. Therefore, more stable oligonucleotide phosphorothioate (Kawasaki et al., *J. Med. Chem.* 36:831-841, 1993) and N3'→P5' phosphoramidates (Schultz et al., *Nucl. Acids Res.*, 24:2966-2973, 1996), which resist enzymatic digestion were prepared. For the former compounds introduction of phosphorothioate linkages resulted in reduction of the duplex stability, whereas for the latter ones synergistic stabilizing effects of both 2'-ribo-fluoro and 3'-amino groups were observed. Additionally, oligo-2'-ribo-fluoro-N3'→P5' phosphoramidates were less acid labile than their 2'-deoxy N3'→P5' phosphoramidate counterparts (Schultz et al., *Nucl. Acids Res.*, 24:2966-2973, 1996).

The oligonucleotide N3'→P5' phosphoramidates form unusually stable duplexes with complementary DNA and especially RNA strands, as well as stable triplexes with DNA duplexes, and they are also resistant to nucleases (Chen et al., *Nucleic Acids Research*, 23:2661-2668, 1995; Gryaznov et al., *Proc. Natl. Acad. Sci.*, 92:5798-5802 1995). Moreover oligonucleotide N3'→P5' phosphoramidates were found to be more potent antisense agents than phosphorothioate derivatives both in vitro and in vivo (Skorski et al., *Proc. Natl. Acad. Sci.*, 94:3966-3971, 1997). At the same time the phosphoramidates apparently have a low affinity to the intra- and extracellular proteins and increased acid liability relative to the natural phosphodiester counterparts (Gryaznov et al., *Nucleic Acids Research*, 24:1508-1514, 1996). These two features of the oligonucleotide phosphoramidates may potentially adversely effect their pharmacological properties for some applications. In particular, the acid stability of an oligonucleotide is an important quality given the desire to use oligonucleotide agents as oral therapeutics.

In order to circumvent the above described problems associated with presently known oligonucleotide analogs, a new class of compounds was sought that embodies the best characteristics from both oligonucleotide phosphoramidates and 2'-ribo-fluoronucleotides. The present invention describes the synthesis, properties and uses of oligonucleotide analogues containing 2'-arabino-fluoronucleosides and internucleoside N3'→P5' phosphoramidate linkages.

SUMMARY OF THE INVENTION

The compositions and methods of the present invention relate to nucleosides and to polynucleotides having contiguous nucleoside subunits joined by intersubunit linkages. In one aspect the present invention relates to 2'-arabino-fluoronucleoside and to polynucleotides comprising a plurality of nucleoside subunits comprising at least one 2'-arabino-fluoronucleoside linked to at least one additional nucleoside subunit by a N3'→P5' phosphoramidate inter-subunit linkage. The polynucleotides of the present invention preferably contain at least one 2'-arabino-fluoronucleoside subunit joined by a N3'→P5' phosphoramidate intersubunit linkage defined by the formula of 3'-[-NH—P(—O)(OR)—O-]-5', wherein R is a positively charged counter ion, hydrogen, or lower alkyl. In a preferred embodiment of the invention, R is hydrogen. The inventive polynucleotides can be composed such that all of the intersubunit linkages are N3'→P5' phosphoramidates. Alternatively, the polynucleotides of the invention contain a second class of intersubunit linkages such as phosphodiester, phosphotriester, methylphosphonate, P3'→N5' phosphoramidate, N3'→P5' thiophosphoramidate, and phosphorothioate linkages.

An exemplary N3'→P5' 2'-arabino-fluoro phosphoramidate oligonucleotide has the formula:

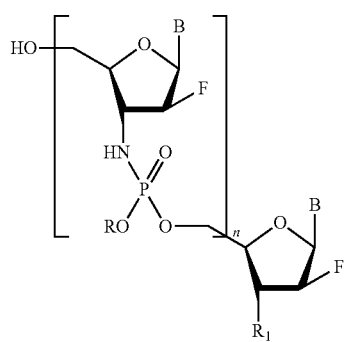

where B is a purine or pyrimidine or an analog thereof, n is an integer between 1 and 49, R is a positively charged counter ion, hydrogen, or lower alkyl, and $R_1$ is selected from the group consisting of hydroxyl, amino and hydrogen. The nucleoside subunits making up the polynucleotides of the present invention can be selected to be in a defined sequence: such as, a sequence of bases complementary to a single-strand nucleic acid target sequence or a sequence that will allow formation of a triplex structure between the polynucleotide and a target duplex. The inventive oligonucleotides having 2'-arabino-fluoro phosphoramidate subunits and N3'→P5' phosphoramidate intersubunit linkages, as described above, have superior resistance to acid hydrolysis, yet retain the same thermal stability as compared to oligonucleotides containing 2'-ribo-fluoronucleotides joined by phosphodiester linkages.

The present invention also includes a method of synthesizing an oligonucleotide containing 2'-arabino-fluoronucleosides and internucleoside N3'→P5' phosphoramidate linkages. In this method a first 3'-amino protected nucleoside is attached to a solid phase support. The protected 3' amino group is then deprotected to form a free 3' amino group to which a second nucleoside is added. The free 3' amino group of the first nucleoside is reacted with a 3'-protected amino-nucleoside-5'-(O-cyanoethyl-N,N-diisopropylamino)-2'-arabino-fluoro phosphoramidite monomer to form an oligonucleotide internucleoside N3'→P5' phosphoramidite linkage. The phoshoramidite linkage is then oxidized to form a phosphoramidate internucleoside linkage.

The present invention also provides 2-arabino-fluoro monomers of formula:

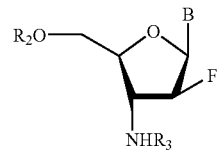

where B is a purine or pyrimidine or an analog thereof; $R_2$ is H, lower alkyl, $PO_3$, or $PN(R_4)_2OR_5$ wherein $R_4$ is dialkyl, and $R_5$ is cyano-lower alkyl; and $R_3$ is hydrogen or substituted or unsubstituted trityl. In one representative embodiment, $R_2$ is $PN(R_4)_2OR_5$ wherein $R_4$ is diisopropyl, $R_5$ is O-cyanoethyl and $R_3$ is monomethoxytrityl, as shown in the formula below:

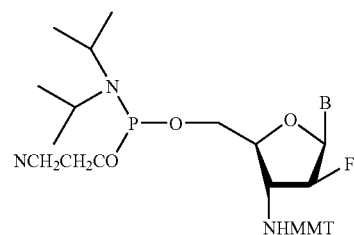

In another embodiment the constituent B is exocyclic amino protected. In other embodiments of the invention, when B is guanine the N2 amino group of guanine is protected with an isobutyl group, when B is 2,6-diaminopurine the exocyclic amine groups are protected with a phenoxyancetyl group, and when B is cytosine the N4 amino group of cytosine is protected with a benzoyl group.

In another embodiment of the invention, a method is provided for hybridizing a 2'-arabino-fluoro oligonucleotide N3'→P5' phosphoramidate to a nucleic acid target. First a polynucleotide comprising a defined sequence of nucleoside subunits defined by the formula:

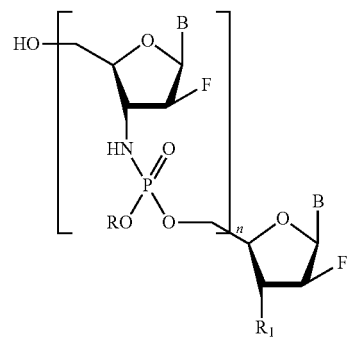

where B is a purine or pyrimidine or an analog thereof, n is an integer between 1 and 49 and $R_1$ is selected from the group consisting of hydroxyl, amino and hydrogen. The 2' arabino-fluoro N3'→P5' phosphoramidate polynucleotide is then contacted with the nucleic acid target to allow formation of a hybridization complex between the polynucleotide and the nucleic acid target.

The present invention also includes pharmaceutical compositions and kits for the isolation of a target RNA that include a polynucleotide having at least one 2'-arabino-fluoronucleoside and phosphoramidate N3'→P5' linkage, as described above. The inventive oligonucleotides are particularly useful in oral therapeutic applications based on hybridization, such as, antigene and antisense applications, including the inhibition of telomerase enzyme.

DETAILED DESCRIPTION OF THE PREFERRED EMBODIMENT

Definitions

Figure 1:
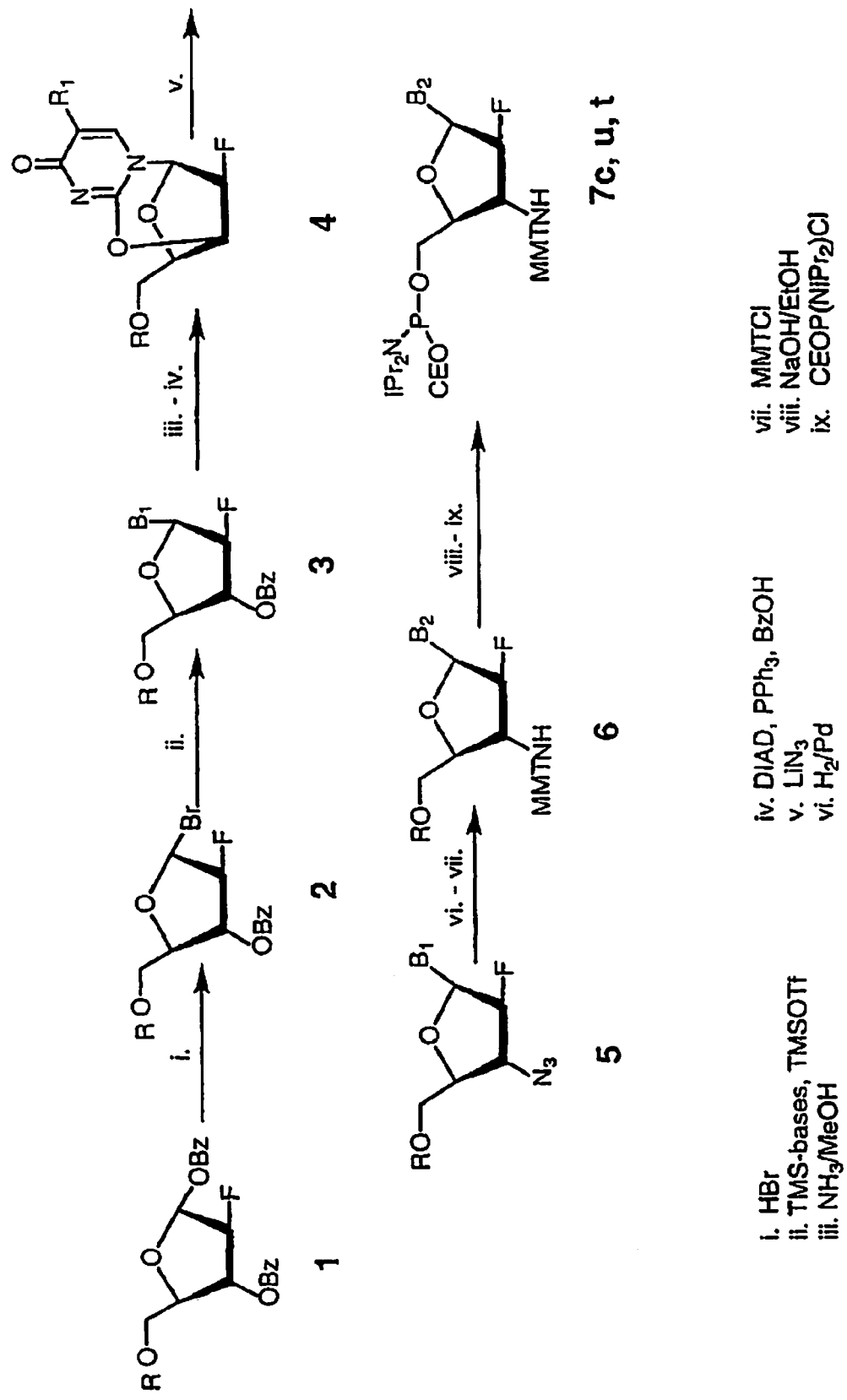
FIG. 1 shows a schematic outline of the step-by-step synthesis of 2-arabino-fluoronucleoside monomers, $B_1$ corresponds to thymine or uracil, $B_2$ corresponds to thymine, uracil or $N^4$-benzoyl-cytosine and R1 is hydrogen or methyl.

An "alkyl group" refers to an alkyl or substituted alkyl group having 1 to 20 carbon atoms, such as methyl, ethyl, propyl, and the like. Lower alkyl typically refers to $C_1$ to $C_5$. Intermediate alkyl typically refers to $C_6$ to $C_{10}$.

An "aryl group" refers to an aromatic ring group having 5-20 carbon atoms, such as phenyl, naphthyl, anthryl, or substituted aryl groups, such as alkyl- or aryl-substitutions like tolyl, ethylphenyl, biphenylyl, etc. Also included are heterocyclic aromatic ring groups having one or more nitrogen, oxygen, or sulfur atoms in the ring.

A "positively charged counter ion" refers to any ion capable of forming an ion pair with oxygen, such a $Na^+$, $K^+$, $Ca^+$, $Mg^{2+}$, $Mn^{2+}$ and the like.

"Oligonucleotides" typically refer to nucleoside subunit polymers having between about 2 and about 50 contiguous subunits. The nucleoside subunits can be joined by a variety of intersubunit linkages, including, but not limited to, those shown in FIGS. 1A to 1C. Further, "oligonucleotides" includes modifications, known to one skilled in the art, to the sugar backbone (e.g., ribose or deoxyribose subunits), the sugar (e.g., 2' substitutions), the base, and the 3' and 5' termini. The term "polynucleotide", as used herein, has the same meaning as "oligonucleotide" is used interchangeably with "polynucleotide".

Whenever an oligonucleotide is represented by a sequence of letters, such as "ATGUCCTG," it will be understood that the nucleotides are in 5'→3' order from left to right and that "A" denotes deoxyadenosine, "C" denotes deoxycytidine, "G" denotes deoxyguanosine, "T" denotes thymidine, and "U" denotes deoxyuridine, unless otherwise noted.

As used herein, "nucleoside" includes the natural nucleosides, including 2'-deoxy and 2'-hydroxyl forms, e.g., as described in Kornberg and Baker, *DNA Replication*, 2nd Ed. (Freeman, San Francisco, 1992). "Analogs" in reference to nucleosides includes synthetic nucleosides having modified base moieties and/or modified sugar moieties, e.g., described generally by Scheit, *Nucleotide Analogs* (John Wiley, New York, 1980). Such analogs include synthetic nucleosides designed to enhance binding properties, e.g., stability, specificity, or the like, such as disclosed by Uhlmann and Peyman (*Chemical Reviews*, 90:543-584, 1990).

A "base" is defined herein to include (i) typical DNA and RNA bases (uracil, thymine, adenine, guanine, and cytosine), and (ii) modified bases or base analogs (e.g., 5-methyl-cytosine, 5-bromouracil, or inosine). A base analog is a chemical whose molecular structure mimics that of a typical DNA or RNA base.

As used herein, "pyrimidine" means the pyrimidines occurring in natural nucleosides, including cytosine, thymine, and uracil, and common analogs thereof, such as those containing oxy, methyl, propynyl, methoxy, hydroxyl, amino, thio, halo, and like substituents. The term as used herein further includes pyrimidines with common protection groups attached, such as $N_4$-benzoylcytosine. Further common pyrimidine protection groups are disclosed by Beaucage and Iyer (*Tetrahedron* 48:223-2311, 1992).

As used herein, "purine" means the purines occurring in natural nucleosides, including adenine, guanine, and hypoxanthine, and common analogs thereof, such as those containing oxy, methyl, propynyl, methoxy, hydroxyl, amino, thio, halo, and like substituents. The term as used herein further includes purines with common protection groups attached, such as $N_2$-benzoylguanine, $N_2$-isobutyrylguanine, $N_6$-benzoyladenine, and the like. Further common purine protection groups are disclosed by Beaucage and Iyer (cited above).

As used herein, the term "protected" as a component of a chemical name refers to art-recognized protection groups for a particular moiety of a compound, e.g., "5'-protected-hydroxyl" in reference to a nucleoside includes triphenylmethyl (i.e., trityl), p-anisyldiphenylmethyl (i.e., monomethoxytrityl or MMT), di-p-anisylphenylmethyl (i.e., dimethoxytrityl or DMT), and the like. Art-recognized protection groups are described in the following references: Gait, editor, *Oligonucleotide Synthesis: A Practical Approach* (IRL Press, Oxford, 1984); Amamath and Broom, *Chemical Reviews*, 77:183-217, 1977; Pon et al., *Biotechniques*, 6:768-775, 1988; Ohtsuka et al., *Nucleic Acids Research*, 10:6553-6570, 1982; Eckstein, editor, *Oligonucleotides and Analogues: A Practical Approach* (IRL Press, Oxford, 1991), Greene and Wuts, *Protective Groups in Organic Synthesis*, Second Edition (John Wiley & Sons, New York, 1991), Narang, editor, *Synthesis and Applications of DNA and RNA* (Academic Press, New York, 1987), Beaucage and Iyer (cited above), and like references.

As used herein, "stringency" refers to the hybridization conditions under which an oligonucleotide binds to a nucleic acids to which it has sequence homology, i.e. a "target nucleic acid." It is understood that an oligonucleotide need not be 100% complementary to its target nucleic acid sequence to be specifically hybridizable. An oligonucleotide is specifically hybridizable when binding of oligonucleotide to the target interferes with the normal function of the target molecule to cause a loss of utility, and there is a sufficient degree of complementarity to avoid nonspecific binding of oligonucleotide to non-target sequences under conditions in which specific binding is desired, i.e., under physiological conditions in the case of in vivo assays or therapeutic treatment or, in the case of in vitro assays, under conditions in which the assays are conducted.

The term "hybridization stringency" is well known in the art and relates to the approximate buffer, salt and temperature conditions under which an oligonucleotide hybridizes specifically to its target nucleic acid. Generally, the following conditions are used to define hybridization stringency: "high stringency" denotes the use of a hybridization or wash solution comprising 10 mM phosphate buffer, pH 7.0, at a range of about 45-55° C. The term "moderate stringency" means use of 10 mM phosphate buffer, pH 7.0, with a salt concentration of about 0.1 to 0.5 M NaCl, at a temperature of between about 30 to 45° C. The term "low stringency" means use of about 10 mM phosphate buffer at about pH 7.0, 1.0 M NaCl at room temperature. Low stringency buffers may also include 10 mM $MgCl_2$. It is well understood in the art of nucleic acid hybridization that many factors, such as temperature, salt and inclusion of other components such as formamide, affect the stringency of hybridization.

The compounds of the present invention may be used to inhibit or reduce enzyme activity, such as reducing the activity of the telomerase enzyme and/or reducing the proliferation of cells having telomerase activity. In these contexts, inhibition or reduction of the enzyme activity or cell proliferation refer to a lower level of the measured activity relative to a control experiment in which the enzyme or cells are not treated with the test compound. In particular embodiments, the inhibition or reduction in the measured activity is at least a 10% reduction or inhibition. One of skill in the art will appreciate that reduction or inhibition of the measured activity of at least 20%, 50%, 75%, 90% or 100% may be preferred for particular applications.

The present invention is directed generally to 2'-arabino-fluorooligonucleosides and to oligonucleotides containing at least one 2'-arabino-fluoronucleoside joined by an internucleoside N3'→P5' phosphoramidate linkage, methods of synthesizing such analog polynucleotides, and methods of using the inventive oligonucleotides as therapeutic compounds and in diagnostics. More particularly, the 2'-arabino-fluorooligonucleotides of the present invention have the formula:

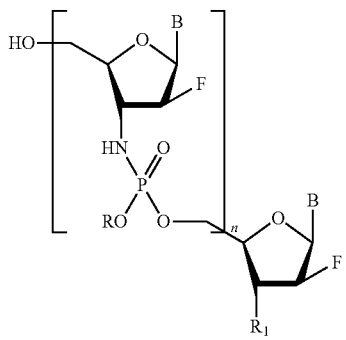

wherein B is a purine or pyrimidine or an analog thereof such as uracil, thymine, adenine, guanine, cytosine, 5-methylcytosine, 5-bromouracil and inosine, R is a positively charged counter ion or hydrogen, $R_1$ is selected from the group consisting of hydroxyl, amino and hydrogen, and n is an integer between 1 and 49.

The nucleoside subunits making up the polynucleotides nucleotides of the present invention can be selected to be in a defined sequence: such as, a sequence of bases complementary to a single-strand nucleic acid target sequence or a sequence that will allow formation of a triplex structure between the polynucleotide and a target duplex.

The inventive oligonucleotides can be used to hybridize to target nucleic acid sequences such as RNA and DNA. When desirable, the oligonucleotides of the present invention can be labeled with a reporter group, such as radioactive labels, biotin labels, fluorescent labels and the like, to facilitate the detection of the polynucleotide itself and its presence in, for example, hybridization complexes.

In another aspect of the invention, a kit for isolating a target nucleic acid from a sample is provided. The kit contains an oligonucleotide having a defined sequence of nucleoside subunits joined by a least one intersubunit linkage defined by the formula:

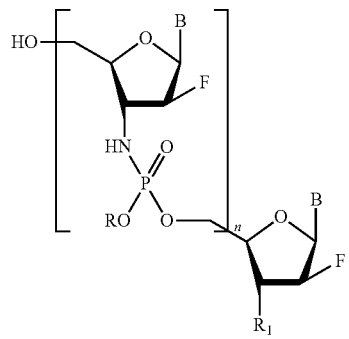

where B is a purine or pyrimidine or an analog thereof, n is an integer between 1 and 49, R is a positively charged counter ion or hydrogen, and $R_1$ is selected from the group consisting of hydroxyl, amino and hydrogen, and wherein the oligonucleotide hybridizes to the target nucleic acid.

In other aspects, the invention is directed to a solid phase method of synthesizing oligonucleotide containing 2'-arabino-fluoronucleosides and internucleoside N3'→P5' phosphoramidate linkages using a modification of the phosphoramidite transfer methodology of Nelson et al. (*J. Organic Chemistry* 62:7278-7287, 1997). The synthetic strategy employed 3'—NH-trityl-protected 3'-aminonucleoside 5'-O-cyanoethyl-N,N-diisopropylaminophosphoramidites (Nelson et al., cited above) that were purchased from Cruachem and JBL Scientific, Inc. (Aston, Pa. and San Luis Obispo, Calif., respectively). Every synthetic cycle was conducted using the following chemical steps: 1) detritylation, 2) coupling; 3) capping, and 4) oxidizing.

Chimeric 2'-arabino-fluoro N3'→P5'-thiophosphoramidate oligonucleotides can be made by substitution of a sulfurization reaction in place of the oxidation reaction at synthetic step 4 above, which results in formation of a thio-phosphoramidate mixed oligonucleotide (see Pongracz, et al., *Tetrahedron*, 40:7661-7664, 1999). In addition, chimeric oligonucleotides can be made comprising 2'-ribo-fluoro (see Schultz, et al., *Nucl. Acids Res.*, 24:2966-2973, 1996) and 2'-arabino-fluoro phosphoramidates, and thio-N3'→P5'-phosphoramidates with 2'-arabino-fluoronucleosides. Similarly, phosphodiester-2'-arabino-fluoro phosphoramidates can be made by using 5'-phosphoramidite-3'-O-DMTr-protected nucleotides as monomeric building blocks. These synthetic approaches are known in the art (see Pongracz, et al., 1999 and Schultz, et al., 1996.).

In another embodiment of the present invention, the acid stability of oligonucleotides is increased by incorporating 2'-arabino-fluoronucleosides subunits lined by N3'→P5' thio-phosphoramidate intersubunit linkages into an oligonucleotide. The hybridization properties of the phosphoramidate 2'-arabino-fluorooligonucleotides were evaluated relative to complementary DNA or RNA strands having phosphodiester or 2'-arabino-ribose phosphoramidate intersubunit linkages. The thermal stability data for duplexes generated from 2'-arabino-ribose phosphoramidate, phosphoramidate, phosphodiester and the inventive 2'-arabino-fluoro phosphoramidate oligonucleotides, are summarized in Example 4, Table 1.

Applications of Oligonucleotides Containing 2-Arabino-Fluoronucleosides and Internucleoside 3'-NHP(O)(O⁻)O-5' Phosphoramidate Linkages 2'-Arabino-fluorooligonucleotide SEQ ID NO:8 phosphoramidate was synthesized (see Table 1). This compound was surprisingly base and acid stable and formed a stable complex with a complementary RNA and DNA target The N3'→P5' phosphoramidate 2'-arabino-fluoro-polynucleotides of the present invention are useful for anti-sense and anti-gene diagnostic/therapeutic applications. In a preferred embodiment of the present invention, the oligonucleotides are oligodeoxyribonucleotides.

A. Telomerase Inhibition Applications

Recently, an understanding of the mechanisms by which normal cells reach the state of senescence, i.e., the loss of proliferative capacity that cells normally undergo in the cellular aging process, has begun to emerge. The DNA at the ends, or telomeres, of the chromosomes of eukaryotes usually consists of tandemly repeated simple sequences. Scientists have long known that telomeres have an important biological role in maintaining chromosome structure and function. More recently, scientists have speculated that the cumulative loss of telomeric DNA over repeated cell divisions may act as a trigger of cellular senescence and aging, and that the regulation of telomerase, an enzyme involved in the maintenance of telomere length, may have important biological implications. See Harley, *Mutation Research*, 256:271-282, 1991. Experiments by Bodnar et al. have confirmed the importance of telomeres and telomerase in controlling the replicative lifespan of cultured normal human cells. See Bodnar et al., *Science* 279:349-352, 1998.

Telomerase is a ribonucleoprotein enzyme that synthesizes one strand of the telomeric DNA using as a template a sequence contained within the RNA component of the enzyme. See Blackburn, *Annu. Rev. Biochem.*, 61:113-129, 1992. The RNA component of human telomerase has been sequenced and is 453 nucleotides in length containing a series of 11-base sequence repeats that is complementary to the telomere repeat. Human telomerase activity has been inhibited by a variety of oligonucleotides complementary to the RNA component of telomerase. See Norton et al., *Nature Biotechnology*, 14:615, 1996; Pitts et al., *Proc. Natl. Acad. Sci.*, 95:11549-11554, 1998; and Glukhov et al., *Bioch. Biophys. Res. Commun.*, 248:368-371, 1999. 2-Arabino-fluoro phosphoramidate oligonucleotides of the present invention are complementary to 10 to 50 nucleotides of telomerase RNA. Preferably, the inventive telomerase inhibitor 2-arabino-fluoro phosphoramidate oligonucleotides have a 10 to 20 consecutive base sequence that are complementary to telomerase RNA.

Methods for detecting telomerase activity, as well as for identifying compounds that regulate or affect telomerase activity, together with methods for therapy and diagnosis of cellular senescence and immortalization by controlling telomere length and telomerase activity, have also been described. See, Feng et al., *Science,* 269:1236-1241, 1995; Kim et al., *Science,* 266:2011-2014, 1994; PCT patent publication No. 93/23572, published Nov. 25, 1993; and U.S. Pat. Nos. 5,656,638, 5,760,062, 5,767,278, 5,770,613 and 5,863,936.

The identification of compounds that inhibit telomerase activity provides important benefits to efforts at treating human disease. Compounds that inhibit telomerase activity can be used to treat telomerase-mediated disorders, such as cancer, since cancer cells express telomerase activity and normal human somatic cells do not possess telomerase activity at biologically relevant levels (i.e., at levels sufficient to maintain telomere length over many cell divisions). Unfortunately, few such compounds, especially compounds with high potency or activity and compounds that are orally bioavailable, have been identified and characterized. Hence, there remains a need for compounds that act as telomerase inhibitors that have relatively high potency or activity and that are orally bioavailable, and for compositions and methods for treating cancer and other diseases in which telomerase activity is present abnormally.

The new phosphoramidate 2'-arabino-fluorooligonucleotide compounds of the present invention are acid and base stable, and therefore, have many valuable uses as inhibitors of deleterious telomerase activity, such as, for example, in the treatment of cancer in humans. Pharmaceutical compositions of phosphoramidate 2'-arabino-fluorooligonucleotide can be employed in treatment regimens in which cancer cells are killed, in vivo, or can be used to kill cancer cells ex vivo. Thus, this invention provides therapeutic compounds and compositions for treating cancer, and methods for treating cancer in mammals (e.g., cows, horses, sheep, steer, pigs and animals of veterinary interest such as cats and dogs). In addition, the phosphoramidate 2'-arabino-fluorooligonucleotides of the present invention may also be used to treat other telomerase-mediated conditions or diseases, such as, for example, other hyperproliferative or autoimmune disorders such as psoriasis, rheumatoid arthritis, immune system disorders requiring immune system suppression, immune system reactions to poison ivy or poison oak, and the like.

As noted above, the immortalization of cells involves inter alia the activation of telomerase. More specifically, the connection between telomerase activity and the ability of many tumor cell lines, including skin, connective tissue, adipose, breast, lung, stomach, pancreas, ovary, cervix, uterus, kidney, bladder, colon, prostate, central nervous system (CNS), retina and blood tumor cell lines, to remain immortal has been demonstrated by analysis of telomerase activity (Kim et al., above). This analysis, supplemented by data that indicates that the shortening of telomere length can provide the signal for replicative senescence in normal cells, see PCT Application No. 93/23572, demonstrates that inhibition of telomerase activity can be an effective anti-cancer therapy. Thus, telomerase activity can prevent the onset of otherwise normal replicative senescence by preventing the normal reduction of telomere length and the concurrent cessation of cell replication that occurs in normal somatic cells after many cell divisions. In cancer cells, where the malignant phenotype is due to loss of cell cycle or growth controls or other genetic damage, an absence of telomerase activity permits the loss of telomeric DNA during cell division, resulting in chromosomal rearrangements and aberrations that lead ultimately to cell death. However, in cancer cells having telomerase activity, telomeric DNA is not lost during cell division, thereby allowing the cancer cells to become immortal, leading to a terminal prognosis for the patient. Agents capable of inhibiting telomerase activity in tumor cells offer therapeutic benefits with respect to a wide variety of cancers and other conditions (e.g., fungal infections) in which immortalized cells having telomerase activity are a factor in disease progression or in which inhibition of telomerase activity is desired for treatment purposes. The telomerase inhibitors of the invention can also be used to inhibit telomerase activity in germ line cells, which may be useful for contraceptive purposes.

In addition, it will be appreciated that therapeutic benefits for treatment of cancer can be realized by combining a telomerase inhibitor of the invention with other anti-cancer agents, including other inhibitors of telomerase such as described in U.S. Pat. Nos. 5,656,638, 5,760,062, 5,767,278, 5,770,613 and 5,863,936. The choice of such combinations will depend on various factors including, but not limited to, the type of disease, the age and general health of the patient, the aggressiveness of disease progression, the TRF length and telomerase activity of the diseased cells to be treated and the ability of the patient to tolerate the agents that comprise the combination. For example, in cases where tumor progression has reached an advanced state, it may be advisable to combine a telomerase inhibiting compound of the invention with other agents and therapeutic regimens that are effective at reducing tumor size (e.g., radiation, surgery, chemotherapy and/or hormonal treatments). In addition, in some cases it may be advisable to combine a telomerase inhibiting agent of the invention with one or more agents that treat the side effects of a disease, e.g., an analgesic, or agents effective to stimulate the patient's own immune response (e.g., colony stimulating factor).

The compounds of the present invention demonstrate inhibitory activity against telomerase activity in vivo, as can be demonstrated as described below. The in vitro activities of the compounds of the invention can also be demonstrated using the methods described herein. As used herein, the term "in vitro" refers to tests performed using living cells in tissue culture. Such procedures are also known as "ex vivo".

One method used to identify phosphoramidate 2'-arabino-fluoro polynucleotides of the invention that inhibit telomerase activity involves placing cells, tissues, or preferably a cellular extract or other preparation containing telomerase in contact with several known concentrations of a phosphoramidate 2'-arabino-fluorooligonucleotide that is complementary to the RNA component of telomerase in a buffer compatible with telomerase activity. The level of telomerase activity for each concentration of the phosphoramidate 2'-arabino-fluoro polynucleotide is measured and the $IC_{50}$ (the concentration of the polynucleotide at which the observed activity for a sample preparation is observed to fall one-half of its original or a control value) for the polynucleotide is determined using standard techniques. Other methods for determining the inhibitory concentration of a compound of the invention against telomerase can be employed as will be apparent to those of skill in the art based on the disclosure herein.

With respect to the treatment of malignant diseases using phosphoramidate 2'-arabino-fluoro polynucleotides that are complementary to the RNA component of telomerase are expected to induce crisis in telomerase-positive cell lines. Treatment of telomerase-positive cell lines, such as HEK-293, HeLa and HME50-5E human breast epithelial cells that were spontaneously immortalized, with a phosphoramidate '-arabino-fluorooligonucleotide that is complementary to the RNA sequence component of telomerase is also expected to induce a reduction of telomere length in the treated cells.

Phosphoramidate 2'-arabino-fluorooligonucleotides of the invention are also expected to induce telomere reduction during cell division in human tumor cell lines, such as the ovarian tumor cell lines OVCAR-5 and SK-OV-3. Importantly, however, in normal human cells used as a control, such as BJ cells of fibroblast origin, the observed reduction in telomere length is expected to be no different from cells treated with a control substance, e.g., a thiophosphoramidate oligonucleotide that has at least one single base mismatch with the complementary telomerase RNA target. The phosphoramidate 2'-arabino-fluorooligonucleotides of the invention also are expected to demonstrate no significant cytotoxic effects at concentrations below about 20 µM in the normal cells.

In addition, the specificity of the phosphoramidate 2'-arabino-fluorooligonucleotides of the present invention for telomerase RNA can be determined by performing hybridization tests with and comparing their activity ($IC_{50}$) with respect to telomerase and to other enzymes known to have essential RNA components. Compounds having lower $IC_{50}$ values for telomerase as compared to the $IC_{50}$ values toward the other enzymes being screened are said to possess specificity for telomerase.

In vivo testing can also be performed using a mouse xenograft model, for example, in which OVCAR-5 tumor cells are grafted onto nude mice, in which mice treated with a phosphoramidate 2'-arabino-fluorooligonucleotide of the invention are expected to have tumor masses that, on average, may increase for a period following the initial dosing, but will begin to shrink in mass with continuing treatment. In contrast, mice treated with a control (e.g., a phosphoramidate 2'-arabino-fluorooligonucleotide that has at least one single base mismatch with the complementary telomerase RNA target) are expected to have tumor masses that continue to increase.

From the foregoing those skilled in the art will appreciate that the present invention also provides methods for selecting treatment regimens involving administration of a phosphoramidate 2'-arabino-fluorooligonucleotide of the invention. For such purposes, it may be helpful to perform a terminal restriction fragment (TRF) analysis in which DNA from tumor cells is analyzed by digestion with restriction enzymes specific for sequences other than the telomeric $(T_2 AG_3)_N$ sequence. Following digestion of the DNA, gel electrophoresis is performed to separate the restriction fragments according to size. The separated fragments are then probed with nucleic acid probes specific for telomeric sequences to determine the lengths of the terminal fragments containing the telomere DNA of the cells in the sample. By measuring the length of telomeric DNA, one can estimate how long a telomerase inhibitor should be administered and whether other methods of therapy (e.g., surgery, chemotherapy and/or radiation) should also be employed. In addition, during treatment, one can test cells to determine whether a decrease in telomere length over progressive cell divisions is occurring to demonstrate treatment efficacy.

Thus, in one aspect, the present invention provides compounds that can serve in the war against cancer as important weapons against many types of malignancies. In particular, the phosphoramidate 2'-arabino-fluoro-polynucleotides of the present invention can provide a highly general method of treating many, if not most, malignancies, as demonstrated by the highly varied human tumor cell lines and tumors having telomerase activity. More importantly, the phosphoramidate 2'-arabino-fluorooligonucleotides of the present invention can be effective in providing treatments that discriminate between malignant and normal cells to a high degree, avoiding many of the deleterious side-effects present with most current chemotherapeutic regimes which rely on agents that kill dividing cells indiscriminately.

B. Antisense Applications

Antisense therapy involves the administration of exogenous oligonucleotides that bind to a target nucleic acid, typically an RNA molecule, located within cells. The term antisense is so given because the oligonucleotides are typically complementary to mRNA molecules ("sense strands") which encode a cellular product.

The phosphoramidate 2'-arabino-fluorooligonucleotides described herein are useful for antisense inhibition of gene expression (Matsukura et al., *Proc. Natl. Acad. Sci.*, 86:4244-4248, 1989; Agrawal et al., *Proc. Natl. Acad. Sci.*, 86:7790-7794, 1989; Zamecnik et al., *Proc. Natl. Acad. Sci.*, 83:4143-4146, 1986; Rittner and Sczakiel, *Nucleic Acids Research*, 19:1421-1426, 1991; Stein and Cheng, *Science*, 261:1004-1012, 1993). N3'→P5' phosphoramidate 2'-arabino-fluorooligonucleotides have therapeutic applications for a large number of medically significant targets, including, but not limited to inhibition of cancer cell proliferation and interference with infectious viruses. The N3'→P5' phosphoramidate 2'-arabino-fluorooligonucleotides are useful for both veterinary and human applications. The high acid stability of the inventive oligonucleotides and their ability to act effectively as antisense molecules at low concentrations (see below) make these oligonucleotides highly desirable as therapeutic antisense agents.

Anti-sense agents typically need to continuously bind all target RNA molecules so as to inactivate them or alternatively provide a substrate for endogenous ribonuclease H (RNase H) activity. Sensitivity of RNA/oligonucleotide complexes, generated by the methods of the present invention, to RNase H digestion can be evaluated by standard methods (Donia et al., *J. Biol. Chem.*, 268:14514-14522, 1993; Kawasaki et al., *J. Medicinal Chem.*, 36:831-841, 1993).

The methods of the present invention provide several advantages over the more conventional antisense agents. First, phosphoramidate 2'-arabino-fluorooligonucleotides bind more strongly to RNA targets as corresponding phosphodiester, oligonucleotides. Second, the phosphoramidate 2'-arabino-fluorooligonucleotides are more resistant to degradation by cellular nucleases and by acid or base conditions. Further, when an RNA is coded by a mostly purine strand of a duplex target sequence, 2'-arabino-fluoro phosphoramidate analog oligonucleotides targeted to the duplex also have potential for inactivating the DNA—i.e., the ability to inactivate a pathogen in both single-stranded and double-stranded forms (see discussion of anti-gene therapies below). Lastly, the oligonucleotides of the present invention form more stable triple stranded structures when annealed to double stranded DNA targets than do natural phosphodiester linked oligonucleotides.

Sequence-specific phosphoramidate 2'-arabino-fluorooligonucleotide molecules are potentially powerful therapeutics for essentially any disease or condition that in some way involves RNA. Exemplary modes by which such sequences can be targeted for therapeutic applications include:

a) targeting RNA sequences expressing products involved in the propagation and/or maintenance infectious agents, such as, bacteria, viruses, yeast and other fungi, for example, a specific mRNA encoded by an infectious agent;

b) formation of a duplex molecule that results in inducing the cleavage of the RNA (e.g., RNase H cleavage of RNA/DNA hybrid duplex molecules). This is an important property of the inventive 2'-arabino-fluoro phosphoramidate oligonucleotides because, in general, phosphoramidates are not good substrates for RNase H;

c) blocking the interaction of a protein with an RNA sequence (e.g., the interaction of TAT and TAR, see below); and d) targeting sequences causing inappropriate expression or proliferation of cellular genes: for example, genes associated with cell cycle regulation; inflammatory processes; smooth muscle cell (SMC) proliferation, migration and matrix formation (Liu et al., *Circulation*, 79:1374-1387, 1989); certain genetic disorders; and cancers (protooncogenes).

In one embodiment, translation or RNA processing of inappropriately expressed cellular genes is blocked. Exemplary potential target sequences are protooncogenes, for example, including but not limited to the following: c-myc, c-myb, c-fos, c-kit, ras, and BCR/ABL (e.g., Wickstrom, Editor, *Prospects for Antisense Nucleic Acid Therapy of Cancer and AIDS*, Wiley-Liss, New York, N.Y., 1991; Zalewski et al., *Circulation Res.*, 88:1190-1195, 1993; Calabretta et al., *Seminars in Cancer Biol.*, 3:391-398, 1992; Calabretta et al., *Cancer Treatment Rev.* 19:169-179, 1993), oncogenes/tumor suppresser genes (e.g., p53, Bayever et al. *Antisense Research and Development*, 3:383-390, 1993), transcription factors (e.g., NF.kappa.B, Cogswell et al., *J. Immunol.*, 150:2794-2804, 1993) and viral genes (e.g., papillomaviruses, Cowsert et al. *Antimicrob. Agents and Chemo.*, 37:171-177, 1993; herpes simplex virus, Kulka et al. *Antiviral Res.*, 20:115-130, 1993). To further illustrate, two RNA regions of the HIV-1 protein that can be targeted by the methods of the present invention are the REV-protein response element (RRE) and the TAT-protein transactivation response element (TAR). REV activity requires the presence of the REV response element (RRE), located in the HIV envelope gene (Malim et al., *Nature*, 338:254-257, 1989; Malim et al., *Cell*, 58:205-214, 1989).

The RRE has been mapped to a 234-nucleotide region thought to form four stem-loop structures and one branched stem-loop structure (Malim et al., *Nature*, 338:254-257, 1989). Data obtained from footprinting studies (Holland et al., *J. Virol.*, 64:5966-5975, 1990; Kjems et al., *Proc. Natl. Acad. Sci.*, 88:683-687, 1991) suggest that REV binds to six base pairs in one stem structure and to three nucleotides in an adjacent stem-loop structure of the RRE. A minimum REV binding region of about 40 nucleotides in stem-loop II has been identified by Cook et al. (*Nucleic Acids Research*, 19:1577-1583). This binding region can be target for generation of RNA/DNA duplexes (e.g., Li et al., *J. Virol.*, 67:6882-6888, 1993) using one or more phosphoramidate 2'-arabino-fluorooligonucleotides, according to the methods of the present invention.

The HIV-1 TAT is essential for viral replication and is a potent transactivator of long terminal repeat (LTR)-directed viral gene expression (Dayton et al., *Cell*, 44:941-947, 1986; Fisher et al., *Nature*, 320:367-371, 1986). Transactivation induced by TAT protein requires the presence of the TAR element (see U.S. Pat. No. 5,837,835) which is located in the untranslated 5' end of the viral mRNA element.

The TAR element is capable of forming a stable stem-loop structure (Muesing et al., *Cell*, 48:691-701, 1987). The integrity of the stem and a 3 nucleotide (nt) bulge on the stem of TAR has been demonstrated to be essential for specific and high-affinity binding of the TAT protein to the TAR element (Roy et al., *Genes Dev.*, 4:1365-1373, 1990; Cordingley et al.,

*Proc. Natl. Acad. Sci.*, 87:8985-8989, 1990; Dingwall et al., *Proc. Natl. Acad. Sci.*, 86:6925-6929, 1989; Weeks et al., *Science*, 249:1281-1285, 1990). This region can be targeted for anti-sense therapy following the method of the present invention.

In addition to targeting the RNA binding sites of the REV, RRE and TAT proteins, the RNA coding sequences for the REV and TAT proteins themselves can be targeted in order to block expression of the proteins.

Initial screening of N3'→P5' phosphoramidate 2'-arabino-fluorooligonucleotides, directed to bind potential antisense target sites, typically includes testing for the thermal stability of resultant RNA/DNA duplexes. When a phosphoramidate 2'-arabino-fluorooligonucleotide is identified that binds a selected RNA target sequence, the oligonucleotide is further tested for inhibition of RNA function in vitro. Cell culture assays systems are used for such in vitro analysis (e.g., herpes simplex virus, Kulka et al., *Antiviral Res.*, 20:115-130, 1993; HIV-1, Li et al., *J. Virol.*, 67:6882-6888, 1993; Vickers et al., *Nucleic Acids Research*, 19:3359-3368, 1991; coronary smooth muscle cell proliferation in restenosis, Zalewski et al., *Nucleic Acids Research*, 15:1699-1715, 1987; IL-2R, Grigoriev et al., *Proc. Natl. Acad. Sci.*, 90:3501-3505, 1993; c-myb, Baer et al., *Blood*, 79:1319-1326, 1992; c-fos, Cutry et al., *J. Biol. Chem.*, 264:19700-19705, 1989; BCR/ABL, Szczylik et al., *Science*, 253:562-565, 1991).

C. Anti-Gene Applications

Inhibition of gene expression via triplex formation has been previously demonstrated (Cooney et al., *Science*, 241: 456-459, 1989; Orson et al., *Nucleic Acids Research*, 19:3435-3441, 1991; Postel et al., *Proc. Natl. Acad. Sci.*, 88:8227-8231, 1991). The increased stability of triplex structures formed when employing third strand phosphoramidate 2'-arabino-fluorooligonucleotides provides a stronger tool for antigene applications, including veterinary and human therapeutic applications.

A target region of choice is selected based on known sequences using standard rules for triplex formation (Helene and Toulme, *Biochem. Biophys. Acta*, 1049:99-125, 1990). Typically, the phosphoramidate 2'-arabino-fluorooligonucleotide sequence is targeted against double-stranded genetic sequences in which one strand contains predominantly purines and the other strand contains predominantly pyrimidines.

Phosphoramidate 2'-arabino-fluorooligonucleotides of the present invention are tested for triplex formation against a selected duplex target sequences using band shift assays (see for example, U.S. Pat. No. 5,726,297, Example 4). Typically, high percentage polyacrylamide gels are used for band-shift analysis and the levels of denaturing conditions (Ausubel et al., *Current Protocols in Molecular Biology*, Hohn Wiley and Sons, Inc. Media Pa.; Sauer et al. eds., *Methods in Enzymology Protein/DNA Interactions*, Academic Press, 1991; Sambrook et al. in *Molecular Cloning: A Laboratory Manual*, Cold Spring Harbor Press, Vol. 2, 1989) are adjusted to reduce any non-specific background binding.

The duplex target is labeled (for example, using a radioactive nucleotide) and mixed with a third strand oligonucleotide, being tested for its ability to form triplex structures with the target duplex. A shift of the mobility of the labeled duplex oligonucleotide indicates the ability of the oligonucleotide to form triplex structures.

Triplex formation is indicated in the band shift assay by a decreased mobility in the gel of the labeled triplex structure relative to the labeled duplex structure.

Numerous potential target sites can be evaluated by this method including target sites selected from a full range of DNA sequences that vary in length as well as complexity. Sequence-specific phosphoramidate 2'-arabino-fluorooligonucleotide molecules are potentially powerful therapeutics for essentially any disease or condition that in some way involves DNA. Exemplary target sequences for such therapeutics include: a) DNA sequences involved in the propagation and/or maintenance infectious agents, such as, bacterial, viruses, yeast and other fungi, for example, disrupting the metabolism of an infectious agent; and b) sequences causing inappropriate expression or proliferation of cellular genes, such as oncogenes, for example, blocking or reducing the transcription of inappropriately expressed cellular genes (such as genes associated with certain genetic disorders).

Gene expression or replication can be blocked by generating triplex structures in regions to which required regulatory proteins (or molecules) are known to bind (for example, HIV transcription associated factors like promoter initiation sites and SP1 binding sites, McShan et al., *J. Biol. Chem.*, 267: 5712-5721, 1992). Alternatively, specific sequences within protein-coding regions of genes (e.g., oncogenes) can be targeted as well.

When a phosphoramidate 2'-arabino-fluorooligonucleotide is identified that binds a selected duplex target sequence tests, for example, by the gel band shift mobility assay described above, the analog is further tested for its ability to form stable triplex structures in vitro. Cell culture and in vivo assay systems, such as those described in U.S. Pat. No. 5,631, 135 are used.

Target sites can be chosen in the control region of the genes, e.g., in the transcription initiation site or binding regions of regulatory proteins (Helene and Toulme, 1990; Birg et al., 1990; Postel et al., 1991; Cooney et al., 1988). Also, target sites can be chosen such that the target also exists in mRNA sequences (i.e., a transcribed sequence), allowing oligonucleotides directed against the site to function as antisense mediators as well (see above).

Also, phosphoramidate 2'-arabino-fluorooligonucleotide molecules can be used to generate triplex molecules with a third strand target (i.e., a single-strand nucleic acid). For example, a DNA molecule having two regions capable of forming a triplex structure with a selected target third strand molecule can be synthesized. Typically the two regions are linked by a flexible region which allows the association of the two regions with the third strand to form a triplex.

Hinge regions can comprise any flexible linkage that keeps the two triplex forming regions together and allows them to associate with the third strand to form the triplex. Third strand targets are selected to have appropriate purine/pyrimidine content so as to allow formation of triplex molecules.

The flexible linkage may connect the two triplex forming regions (typically, complementary DNA strands) in any selected orientation depending on the nature of the base sequence of the target. For example, the two triplex forming regions each have 5' and 3' ends, these ends can be connected by the flexible hinge region in the following orientations: 5' to 3', 3' to 5', 3' to 3', and 5' to 5'.

Further, duplex DNA molecules containing at least one phosphoramidate 2'-arabino-fluoro nucleotide in each strand can be used as decoy molecules for transcription factors or DNA binding proteins (e.g., c-myb).

Single-stranded DNA can also be used as a target nucleic acid for oligonucleotides of the present invention, using, for example, phosphoramidate 2'-arabino-fluorooligonucleotide-containing hairpin structures. Two phosphoramidate 2'-arabino-fluorooligonucleotides can be selected for single-strand DNA target-directed binding. Binding of the two phosphoramidate 2'-arabino-fluorooligonucleotides to the single-strand DNA target results in formation of a triplex.

D. Pharmaceutical Compositions

The present invention includes pharmaceutical compositions useful in antisense and antigene therapies. The compositions comprise an effective amount of N3'→P5' phosphoramidate 2'-arabino-fluorooligonucleotides in combination with a pharmaceutically acceptable carrier. One or more N3'→P5' phosphoramidate 2'-arabino-fluorooligonucleotides (having different base sequences) may be included in any given formulation. In addition, the 2'-arabino-fluorooligonucleotides of the present invention may also be used in combination with one or more other oligonucleotides that lack 2'-arabino-fluoro analog phosphoramidate nucleosides.

The N3'→P5' phosphoramidate 2'-arabino-fluorooligonucleotides, when employed in therapeutic applications, can be formulated neat or with the addition of a pharmaceutical carrier. The pharmaceutical carrier may be solid or liquid. The formulation is then administered in a therapeutically effective dose to a subject in need thereof.

Liquid carriers can be used in the preparation of solutions, emulsions, suspensions and pressurized compositions. The N3'→P5' phosphoramidate 2'-arabino-fluorooligonucleotides are dissolved or suspended in a pharmaceutically acceptable liquid carrier such as water, an organic solvent, a mixture of both, or pharmaceutically accepted oils or fats. The liquid carrier can contain other suitable pharmaceutical additives including, but not limited to, the following: solubilizers, suspending agents, emulsifiers, buffers, thickening agents, colors, viscosity regulators, preservatives, stabilizers and osmolarity regulators. Suitable examples of liquid carriers for parenteral administration of N3'→P5' phosphoramidate 2'-arabino-fluorooligonucleotides preparations include water (partially containing additives, e.g., cellulose derivatives, preferably sodium carboxymethyl cellulose solution), alcohols (including monohydric alcohols and polyhydric alcohols, e.g., glycols) and their derivatives, and oils (e.g., fractionated coconut oil and arachis oil).

For parenteral administration of N3'→P5' phosphoramidate 2'-arabino-fluorooligonucleotides the carrier can also be an oily ester such as ethyl oleate and isopropyl myristate. Sterile carriers are useful in sterile liquid form compositions for parenteral administration.

Sterile liquid pharmaceutical compositions, solutions or suspensions can be utilized by, for example, intraperitoneal injection, subcutaneous injection, intravenously, or topically. For example, antisense oligonucleotides directed against retinal cytomegalovirus infection may be administered topically by eyedrops. N3'→P5' phosphoramidate 2'-arabino-fluorooligonucleotides can be also be administered intravascularly or via a vascular stent impregnated with mycophenolic acid, for example, during balloon catheterization to provide localized anti-restenosis effects immediately following injury.

The liquid carrier for pressurized compositions can be halogenated hydrocarbon or other pharmaceutically acceptable propellant. Such pressurized compositions may also be lipid encapsulated for delivery via inhalation. For administration by intranasal or intrabronchial inhalation or insufflation, N3'→P5' phosphoramidate 2'-arabino-fluorooligonucleotides may be formulated into an aqueous or partially aqueous solution, which can then be utilized in the form of an aerosol, for example, for treatment of infections of the lungs like *Pneumocystis carnii*.

N3'→P5' phosphoramidate 2'-arabino-fluorooligonucleotides may be administered topically as a solution, cream, or lotion, by formulation with pharmaceutically acceptable vehicles containing the active compound. For example, for the treatment of genital warts.

The N3'→P5' phosphoramidate 2'-arabino-fluorooligonucleotides may be administered in liposome carriers. The use of liposomes to facilitate cellular uptake is described, for example, in U.S. Pat. Nos. 4,897,355 (D. Eppstein et al., issued 30 Jan. 1990) and U.S. Pat. No. 4,394,448 (F. Szoka et al., issued 19 Jul. 1983). Numerous publications describe the formulation and preparation of liposomes.

The dosage requirements for treatment with N3'→P5' phosphoramidate 2'-arabino-fluorooligonucleotides vary with the particular compositions employed, the route of administration, the severity of the symptoms presented, the form of N3'→P5' phosphoramidate 2'-arabino-fluorooligonucleotides and the particular subject being treated.

In general, N3'→P5' phosphoramidate 2'-arabino-fluorooligonucleotides are administered at a concentration that affords effective results without causing any harmful or deleterious side effects (e.g., an effective amount). Such a concentration can be achieved by administration of either a single unit dose, or by the administration of the dose divided into convenient subunits at suitable intervals throughout the day.

E. Diagnostic Applications

The phosphoramidate 2'-arabino-fluorooligonucleotides of the present invention are also useful in diagnostic assays for detection of RNA or DNA having a given target sequence. In one general application, the phosphoramidate 2'-arabino-fluorooligonucleotides are labeled (e.g., isotopically or other detectable reporter group) and used as probes for nucleic acid samples that bound to a solid support (e.g., nylon membranes).

Alternatively, the phosphoramidate 2'-arabino-fluorooligonucleotides may be bound to a solid support (for example, magnetic beads) and homologous RNA or DNA molecules in a sample separated from other components of the sample based on their hybridization to the immobilized phosphoramidate analogs. Binding of phosphoramidate 2'-arabino-fluorooligonucleotides to a solid support can be carried out by conventional methods. Presence of the bound RNA or DNA can be detected by standard methods, for example, using a second labeled reporter or polymerase chain reaction (see U.S. Pat. Nos. 4,683,195 and 4,683,202).

Diagnostic assays can be carried out according to standard procedures, with suitable adjustment of the hybridization conditions to allow phosphoramidate 2'-arabino-fluorooligonucleotide hybridization to the target region. The ability of phosphoramidate 2'-arabino-fluorooligonucleotides to bind at elevated temperature can also help minimizes competition for binding to a target sequence between the phosphoramidate 2'-arabino-fluorooligonucleotides probe and any corresponding single-strand phosphodiester oligonucleotide that is present in the diagnostic sample.

F. Other Applications

In one aspect, the phosphoramidate 2'-arabino-fluorooligonucleotides can be used in methods to enhance isolation of RNA or DNA from samples. For example, as discussed above, phosphoramidate 2'-arabino-fluorooligonucleotides can be fixed to a solid support and used to isolate complementary nucleic acid sequences, for example, purification of a specific mRNA from a polyA fraction (Goldberg et al., *Methods in Enzymology*, 68:206, 1979). The phosphoramidate 2'-arabino-fluorooligonucleotides are advantageous for such applications since they can form more stable interactions with RNA and duplex DNA than standard phosphodiester oligonucleotides.

A large number of applications in molecular biology can be found for reporter labeled phosphoramidate 2'-arabino-fluorooligonucleotides, particularly for the detection of RNA in samples. Phosphoramidate 2'-arabino-fluorooligonucleotides can be labeled with radioactive reporters (3H, $^{14}$C, $^{32}$P, or $^{35}$S nucleosides), biotin or fluorescent labels (Gryaznov et al., *Nucleic Acids Research*, 20:3403-3409, 1992). Labeled phosphoramidate 2'-arabino-fluorooligonucleotides can be used as efficient probes in, for example, RNA hybridization reactions (Ausubel et al., *Current Protocols in Molecular Biology*, Hohn Wiley and Sons, Inc., Media, Pa.; Sambrook et al., in *Molecular Cloning: A Laboratory Manual*, Cold Spring Harbor Laboratory Press, Vol. 2, 1989).

Also, double-stranded DNA molecules where each strand contains at least one phosphoramidate 2'-arabino-fluoronucleotide can be used for the isolation of DNA-duplex binding proteins. In this embodiment a duplex containing phosphoramidate 2'-arabino-fluorooligonucleotide is typically affixed to a solid support and sample containing a suspected binding protein is then passed over the support under buffer conditions that facilitate the binding of the protein to its DNA target. The protein is typically eluted from the column by changing buffer conditions.

The triplex forming DNA molecules described above, containing phosphoramidate 2'-arabino-fluorooligonucleotides, can be used as diagnostic reagents as well, to, for example, detect the presence of an RNA molecule in a sample.

Further, complexes containing oligonucleotides having N3'→P5' phosphoramidate 2'-arabino-fluoro nucleotides can be used to screen for useful small molecules or binding proteins: for example, N3'→P5' phosphoramidate 2'-arabino-fluorooligonucleotide complexes with duplex DNA can be used to screen for small molecules capable of further stabilizing the triplex structure. Similar screens are useful with N3'→P5' phosphoramidate 2'-arabino-fluorooligonucleotide complexes formed with single strand DNA and RNA molecules.

G. Variations

Variations on the phosphoramidate 2'-arabino-fluorooligonucleotides used in the methods of the present invention include modifications to facilitate uptake of the oligonucleotide by the cell (e.g., the addition of a cholesterol moiety (Letsinger, U.S. Pat. No. 4,958,013); production of chimeric oligonucleotides using other intersubunit linkages (Goodchild, *Bioconjugate Chem.*, 1:165-187, 1990); modification with intercalating agents (for example, triplex stabilizing intercalating agents, Wilson et al., *Biochemistry*, 32:10614-10621, 1993); and the use of ribose instead of deoxyribose subunits. Further modifications include, 5' and 3' terminal modifications to the oligonucleotides (e.g., —OH, —OR, —NHR, NH$_2$ and cholesterol).

N3'→P5' phosphoramidate 2'-arabino-fluorooligonucleotides may also be modified by conjugation to a polypeptide that is taken up by specific cells. Such useful polypeptides include peptide hormones, antigens and antibodies. For example, a polypeptide can be selected that is specifically taken up by a neoplastic cell, resulting in specific delivery of N3'→P5' phosphoramidate 2'-arabino-fluorooligonucleotides to that cell type. The polypeptide and oligonucleotide can be coupled by means known in the art (see, for example, PCT International Application Publication No. PCT/US89/02363, WO8912110, published Dec. 14, 1989, Ramachandr, K. et al.).

The properties of such modified phosphoramidate 2'-arabino-fluorooligonucleotides, when applied to the methods of the present invention, can be determined by the methods described herein.

Example 1

General Methods $^{31}$P NMR spectra were obtained on a Varian 400 MHz spectrometer. $^{31}$P NMR spectra were referenced against 85% aqueous phosphoric acid. Anion exchange HPLC was performed using a Dionex DX 500 Chromatography System, with a Pharmacia Biotech Mono Q HR 5/5 or 10/16 ion exchange columns. Ion exchange HPLC was performed on the Dionex DX 500 system, using a Pharmacia Mono Q HR 5/5 column. Buffer A and B were: 10 mM NaOH, pH12 and 10 mM NaOH, 1.5 M NaCl, pH12, respectively. Oligonucleotides were eluted using a 1.5%/min. linear gradient of buffer B in A; flow 0.5 mL/min. Mass spectral analysis was performed by Mass Consortium, San Diego, Calif. MALDI-TOF analysis of oligonucleotides was obtained using a PerSpective Biosystems Voyager Elite mass spectrometer, with delayed extraction. Thermal dissociation experiments were conducted on a Cary Bio 100 UV-Vis spectrometer.

All reactions were carried out in oven dried glassware under a nitrogen atmosphere unless otherwise stated. Commercially available DNA synthesis reagents were purchased from Glen Research (Sterling, Va.). Anhydrous pyridine, toluene, dichloromethane, diisopropylethyl amine, triethylamine, acetic anhydride, 1,2-dichloroethane, and dioxane were purchased from Aldrich (Milwaukee, Wis.).

All non-2'-arabino-fluorooligonucleotides were synthesized on an ABI 392 or 394 DNA synthesizer using standard protocols for the phosphoramidite based coupling approach (Caruthers, *Acc. Chem. Res.*, 24:278-284, 1991). The chain assembly cycle for the synthesis of oligonucleotide phosphoramidates was the following: (i) detritylation, 3% trichloroacetic acid in dichloromethane, 1 min.; (ii) coupling, 0.1 M phosphoramidite and 0.45 M tetrazole in acetonitrile, 1-3 min.; (iii) capping, 0.5 M isobutyic anhydride in THF/lutidine, 1/1, v/v, 15 sec; and (iv) oxidation, 0.1 M iodine in THF/pyridine/water, 10/10/1, v/v/v, 30 sec.

Chemical steps within the cycle were followed by acetonitrile washing and flushing with dry argon for 0.2-0.4 min. Cleavage from the support and removal of base and phosphoramidate protecting groups was achieved by treatment with ammonia/EtOH, 3/1, v/v, for 6 h at 55° C. The oligonucleotides were concentrated to dryness in vacuo after which the 2'-t-butyldimethylsilyl groups were removed by treatment with 1M TBAF in THF for 4-16 h at 25° C. The reaction mixtures were diluted with water and filtered through a 0.45 nylon acrodisc (from Gelman Sciences, Ann Arbor, Mich.). Oligonucleotides were then analyzed and purified by Ion Exchange HPLC and finally desalted using gel filtration on a Pharmacia NAP-5 or NAP-25 column.

Example 2

Synthesis of 2'-Arabino-Fluoronucleoside Phosphoramidite Monomers

Preparation of the inventive 2'-arabino-fluoronucleoside monomers is described in FIG. 1. First, a 1-α-O-Benzoyl-3, 5-O-benzoyl-2-arabinofluoro-2-deoxyfuranose sugar precursor 1 (FIG. 1) (from Pfanstiehl Laboratories, Inc., Waukegan, Ill.) was converted into a 1-α-Bromo-3,5-O-benzoyl-2-arabinofluoro-2-deoxyfuranose intermediate 2 with retention of sugar C-1 configuration (Berger et al., *Nucl. Acids Res.*, 26:2473-2480, 1998). Compound 2 was used, without isolation, in a S$_N$2-type glycosylation reaction with silylated purine and pyrimidine bases according to the literature procedure (Berger et al., *Nucl. Acids Res.*, 26:2473-2480, 1998), which resulted in formation of 2'-arabinofluoro-3',5'-O-benzoyl nucleosides 3 (FIG. 1). Stereo selectivity of this glycosylation reaction was quite high—more than 90% of the formed nucleoside 3 had the desired α-anomeric configuration, as was judged by $^1$H NMR analysis of crystallized products. Then, 5'- and 3'-O-benzoyl protecting groups of nucleoside 3 were removed, almost quantitatively, by methanolic ammonia, and the resultant 5'-, 3'-hydroxyl groups containing nucleoside product without additional purification was converted into 2,3'-anhydro-2'-arabinofluoro-5'-O-benzoyl nucleosides 4 under Mitsunobu reaction conditions (Czernecki et al., *Synthesis*, 239-240, 1991). The following treatment of the 2,3'-anhydronucleosides with lithium azide resulted in key 2'-arabinofluoro-3'-azido-5'-O-benzoyl precursor 5 (Glinski, et al., *J. Chem. Soc. Chem. Comm.*, 915-916, 1970). These compounds were converted into thymidine and uracil 2'-arabinofluoro-3'-NH-MMT-5'-O-(cyanoethyl-N,N'-diisopropylamino)-phosphoramidites 7 as described in the literature sequence of chemical transformations: catalytic reduction of 3'-azido to 3'-amino group by hydrogen over palladium, followed by 3'-tritylation, 5'-O-deprotection and 5'-O-phosphitylation (Schultz et al., *Nucl. Acids Res.*, 24:2966-2973, 1996). Cytosine phosphoramidite 7c was obtained from the 3'-azido precursor uracil-to-cytosine conversion process analogous to the literature procedure for 3'-azido-2'-ribo-fluoronucleosides (Schultz et al., *Nucl. Acids Res.*, 24:2966-2973, 1996) (FIG. 1). Total yields of the cytosine, thymidine and uracil phosphoramidites 7c,u,t were in the range of 15-20% as calculated based on the starting sugar precursor 1. Structure of the monomers was confirmed by $^1$H, $^{31}$P, $^{19}$F NMR and by mass spectrometric analysis. For example, for thymidine 7, Rp-, Sp-isomers, $^{31}$P NMR, L, PPM (CDCl$_3$) 149.4; 149.8 $^{19}$F NMR L, ppm (CDCl$_3$) two hextets at −190.26 and −190.88). The data for uracil 7 and cystosine 7 is very similar: $^{31}$P NMR, L, PPM (CDCl$_3$) in range of 148-149; $^{19}$F NMR L, ppm (CDCl$_3$) two hextets at about −188 and −191.

2'-Arabino-fluoro-amino purine monomers can also be prepared starting with purine-3'-azido-2'-hydroxyl precursor, or purine-3'—NH-trityl-2'-hydroxyl precursors that are prepared using the following synthesis methods. The first step of the synthesis involved tin(IV) chloride or trimethylsilyl triflate mediated glycosylation of trimethylsilylated nucleobases (Azhayev, et al. (1979) *Nucleic Acids Res.*, 2:2625-2643; Vorbruggen, et al. (1981) *Chem. Ber.*, 114:1234-1255) to a commonly employed sugar precursor 3-azido-1,2-di-O-acetyl-5-O-toluoyl-3-deoxy-D-ribofuranose 10, which was prepared according to literature procedure (Ozols, et al. *Synthesis*, 557-558). Adenine was protected at N$^6$ with a benzoyl group, while guanine was blocked at N$^2$ with an isobutyl group and at O$^6$ with diphenylcarbamate (Zou, et al. (1987) *Can. J. Chem.*, 65:1436-1437). The protection of O$^6$ with this bulky group allows for selective glycosylation to occur at N$^9$ with very little (≦10%) formation of the undesired N$^7$ regioisomer as judged by TLC analysis. 2,6-Diaminopurine was protected at each exocylic amine with a phenoxyacetyl group for all glycosylation reactions with this highly polar purine base analogue (Schulhof, et al. (1987) *Tetrahedron Lett.*, 28:51-54).

Figure 2:
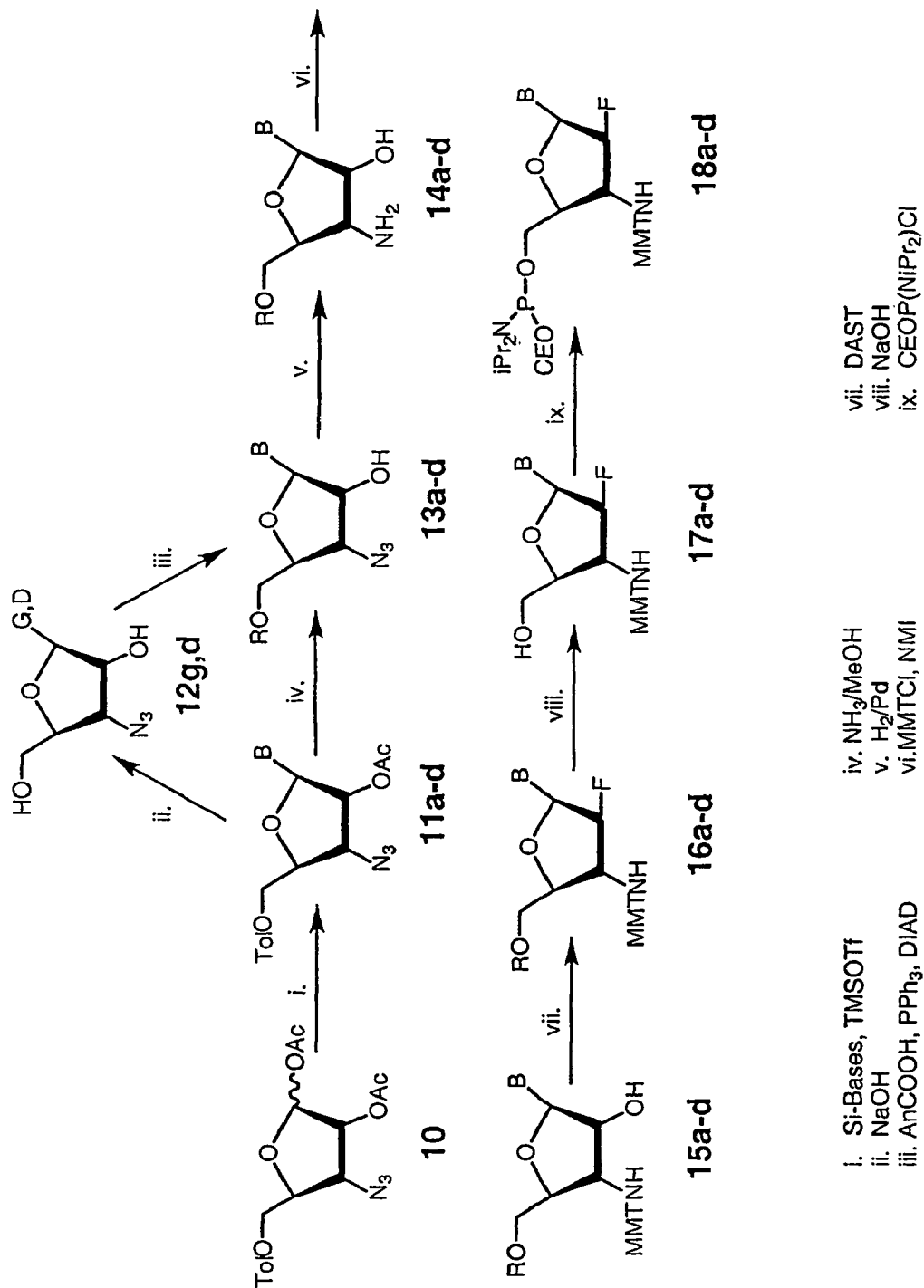
FIG. 2 shows the overall synthetic scheme used to prepare the protected purine 2'-arabino-fluoro phosphoramidite monomers of the present invention. B represents a base selected from the group consisting of adenine (A), guanine (G), and 2,6-diaminopurine (D), uracil (U), cytosine (C) and thymidine (T). Lower case letters a-d associated with compound numbers represent the bases adenine (a), guanine (g), 2,6-diaminopurine (d), uracil (u) and thymine (t). Tol is touoyl, MMTNH is (monomethoxytrityl)amino, $iPr_2N$ is diisopropylamino, and CEO is β-cyanoethyl, R is anisoyl when the base is G or D, and toluoyl when the base is A, T, or U. In addition, when B is adenine the N6 amino group of adenine is protected with a benzoyl group, when B is 2,6-diaminopurine the exocylic amine groups are protected with a phenoxyacetyl group, or when B is guanine the $N^2$ amino group of guanine is protected with an isobutyl group.

Two key synthetic improvements were made to the preparation of the monomers, which allowed for rapid access to the final products with improved overall yields. First, experimental conditions were found which enabled selective removal of the 2'-O-acetyl protecting group in the presence of the 5'-O-toluoyl counterpart (Neilson, et al. (1971) *Can. J. Chem.*, 49:493-498) (FIG. 2). This allowed for the omission of a 5'-hydroxyl reprotection step from the synthetic protocol. Also, a low yielding series of steps late in the monomer synthesis, used in the literature procedure (Gryaznov, et al. (1998) *Nucleic Acids Res.*, 26:4160-4167) to convert a 5'-trityl-nucleoside precursor to the 3'-N-trityl-protected amino intermediate, was also averted. Secondly, following the glycosylation reaction, the next five chemical transformations were conducted with very high yields. This eliminated the need for intermediate purification after steps iv.-viii. (FIG. 2), thus providing a rapid and convenient access to compounds 17a-d. However, it should be noted that for the guanosine and 2,6-diaminopurine analogues, selective removal of the 2'-O-acetyl protecting group was unsuccessful. Thus, both 2'-O and 5'-O-protecting groups were removed, after which the 5'-hydroxyl group was selectively reprotected (FIG. 2).

For compound 11a the 2'-O-acetyl group was selectively removed using 50% (v/v) aqueous ammonia in methanol followed by the 3'-azido group reduction with hydrogen over palladium on carbon. Each of these reactions proceeded with very high, near quantitative, yields as judged by TLC and $^1$H NMR analysis of the products. The 3'-amino group is then protected by treatment with 4-monomethoxytrityl chloride to give compound 15a. The obtained protected nucleoside precursor was then treated with diethylamino sulfur trifluoride (DAST) to make an arabino-fluoro adenine nucleoside 16a. The protected arabino-fluoro product is concentrated in vacuo to which is added 1.0 M NaOH in 65/30/5 pyridine/MeOH/H$_2$O (70 mL) at 0° C. to remove the 5'-O-toluoyl group. The mixture is stirred for 8 min and quenched by addition of saturated NH$_4$Cl. This solution is extracted with ethyl acetate (2×75 mL) and the combined organic layers are dried over Na$_2$SO$_4$, filtered, and concentrated in vacuo. The residue is purified by silica gel chromatography eluting with EtOAc:hexanes (50:50, v/v) to yield 2'-arabino-fluoronucleoside 17a. In an alternative method, the fluoro addition is performed prior to reduction of the 2' azido group to an amino group (e.g. prior to step v. in FIG. 2).

The inability to selectively remove the 2'-O-acetyl group from intermediates 11g and 11d, necessitated the following synthetic protocol. Both 2'-O— and 5'-O-protecting groups were removed with 1 M sodium hydroxide, after which a 5'-O-anisoyl group was selectively reintroduced under Mitsunobu conditions to give 13g and 13d. Compounds 11g and 11d (about 2.8 g, 3.81 mmol) are dissolved in a 1.0 M NaOH solution (65/30/5 pyridine/MeOH/H$_2$O, v/v/v, (40 mL)) at 0° C. The mixtures are stirred for 10 min, and then quenched by addition of saturated NH$_4$Cl (400 mL). The solutions are extracted with CH$_2$Cl$_2$ (5×100 mL) and the combined organic layers are dried over Na$_2$SO$_4$, filtered, and concentrated in vacuo. For guanine nucleosides the residues is triturated well with Et$_2$OH (50 mL) to remove diphenylamine and the resulting material dissolved in acetonitrile (25 mL) and triphenylphosphine (1.2 g, 4.65 mmol). For diaminopurine nucleosides the Na$_2$SO$_4$ dried, filtered and concentrated material is dissolved in dimethylformamide (50 ml) and triphenylphosphine (1.5 g, 5.7 mmol) are added. For the remainder of the steps leading to 13g,d the steps are the same. p-Anisic acid (0.71 g, 4.65 mmol) and diisopropyl azodicarboxylate (0.92 mL, 4.65 mmol) are dissolved in acetonitrile (5 mL) and added dropwise to the reaction mixtures. The solutions are stirred at room temperature for 1 h and was then quenched by pouring them into saturated NaHCO$_3$ (200 mL). The mixtures are extracted with ethyl acetate (200 mL) and after separation the organic phases are washed with saturated NaCl (150 mL). The organic phases are then dried over Na$_2$SO$_4$ and concentrated in vacuo. The residues are purified by silica gel chromatography eluting with a gradient of EtOAc:Hexanes: MeOH (49:49:2, v/v/v to 47.5:47.5:5, v/v/v) to afford 13g,d.

It should be noted that the high reactivity of the 2'-hydroxyl group of the 3'-azido-2'-hydroxyl guanosine intermediate prevented selective reprotection of the 5'-hydroxyl group by either benzoyl chloride or benzoyl anhydride. The same series of steps described above for adinine are used to convert 13 g and 13d into 17g and 17d respectively (FIG. 2). The MMT protecting group in 17a-d can be removed to give the unprotected amino sugar moiety. The 5'-OH group can then be selectively protected with an alkyl group or converted to a mono, di, or triphosphate group. The final step for monomer preparation involves phosphitylation of 17a-d to give the 5'-(2-cyanoethyl-N,N'-diisopropylamino)nucleoside phosphoramidite building blocks 18a-d (FIG. 2).

In order to gain information on the 2'-arabino-fluoro-3'-aminonucleosides sugar puckering, a model N3'→P5' phosphoramidate tri-nucleotide dTn-a(U$^f$nU$^f$n) [SEQ ID NO:1], containing internucleoside and terminal 2'-arabino-fluoro-3'-aminonucleosides ($^{31}$P NMR, L, ppm in D$_2$O 7.8 and 6.7) was synthesized, and the compound was analyzed by high resolution $^1$H and $^{31}$P NMR spectroscopy. The analysis revealed vicinal proton coupling constants J$^3$H1'-H2" of 4.68 Hz for both 2'-arabino-fluoro-uridine nucleosides, and J$^3$H2"-H3' 3.81 Hz and 4.46 Hz for internucleoside and for 3'-terminal 2'-arabino-fluoro-uridines, respectively. The corresponding coupling constants for the prepared model di-nucleoside aU$^f$-pdT [SEQ ID NO:2], containing 2'-arabino-fluoro-3'-hydroxy uracil and the phosphodiester internucleoside bond, were 3.67 Hz and 1.83 Hz respectively, which indicates a significant difference in 3'—NH— and 3'-O-2'-ara-fluoronucleosides sugar puckering. The observed coupling constants for the tri-nucleotide alone do not define the 2'-arabino-fluoro-3'-amino sugars conformation. However, the data obtained from 2D COSY spectra of the tri-nucleotide large intensity of H3'-H4' cross peaks, as well as the data from $^1$H-$^{31}$P 2D heteronuclear spectra (strong H3'-(i-1)P and weak H4'-P cross peaks) suggest prevalence of N-type conformation for the 2'-arabino-fluoro-3'-aminonucleosides. The substitution of 3'-oxygen by 3'-amino group apparently shifts the 2'-arabino-fluoro furanose conformational equilibrium towards N-type, or C3'-endo, for 2'-arabino-fluoronucleosides, which is similar to that for the 2'-deoxy-3'-aminonucleosides.

Example 3

Synthesis of N3'→P5' Phosphoramidite 2'-Arabino-Fluorooligonucleotides

The oligo-2'-arabino-fluoro nucleotide N3'→P5' phosphoramidates were assembled similarly to the oligo-2'-ribofluoro N3'→P5' phosphoramidate compounds. Solid phase synthesis was based on the phosphoramidite transfer reaction using monomer building blocks composed of 5'-(O-cyanoethyl-N,N'-diisopropylamino)-phosphoramidites of 3'-MMTr-protected-3'-amino-2'-arabino-fluoronucleosides (Schultz et al., *Nucl. Acids Res.*, 24:2966-2973, 1996).

The oligonucleotide synthesis was conducted on an automated DNA/RNA ABI 394 synthesizer using the synthetic cycle described before for the 2'-ribo-fluoro phosphoramidites with step-wise coupling yields of about 95-97%. Each of the prepared 2'-arabino-fluorooligonucleotides were synthesized starting from the 5'-end using a support-bound 2'-deoxy-3'-aminonucleoside as the 5'-terminal residue. Coupling steps involved exchange of the diisopropylamino group of the approaching 5'-O-phosphoramidite monomer for the 3'-amino group of the support bound nucleoside. Standard RNA synthesis coupling times (10 min) and activator (1H-tetrazole) were used for each synthetic cycle. Unreacted 3'-amino groups were then capped with isobutyric anhydride, after which oxidation of the internucleotide phosphoramidite diester linkage into the phosphoramidate group was carried out with aqueous iodine. Subsequent detritylation of the 3'-amino group of the added residue enabled additional chain elongation steps to be repeated for the construction of the desired 2'-arabino-fluororooligonucleotide phosphoramidates.

Figure 3:
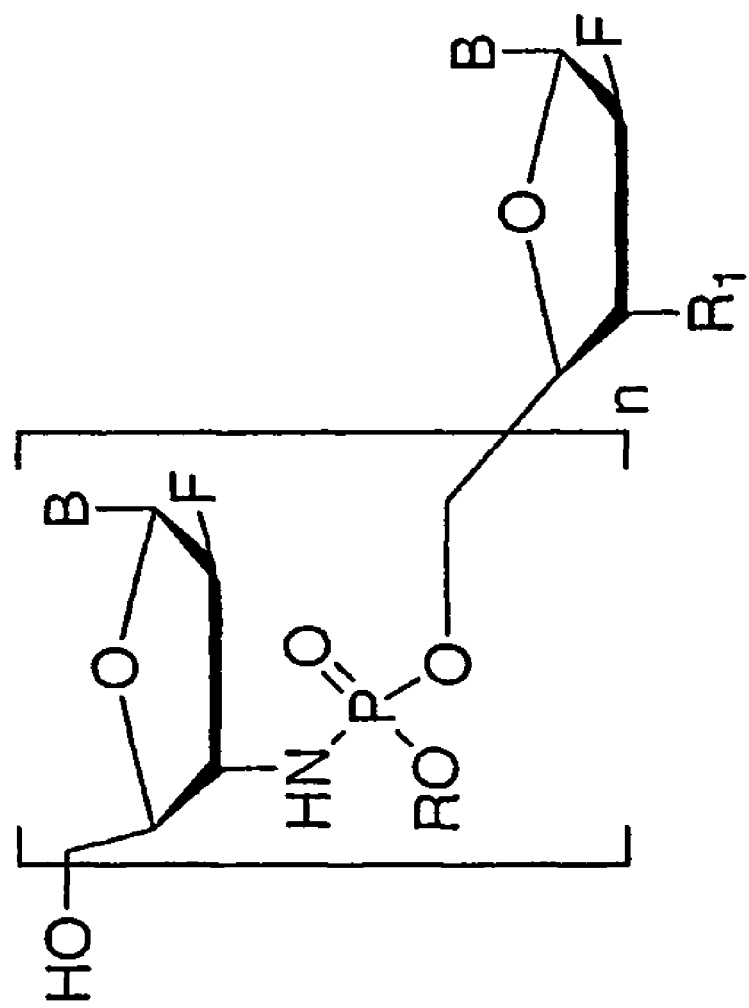
FIG. 3 shows the internucleoside linkage structure of an oligonucleotide containing 2'-arabino-fluoronucleosides joined an internucleoside N3'→P5' phosphoramidate linkage, where R is a positively charged counter ion or hydrogen.

Compounds were cleaved from a solid phase support and all the protective groups were removed with concentrated aqueous ammonia, about 0.5 to 4.5 hours at 55° C. The resulting 2'-arabino-fluorooligonucleotide N3'→P5' phosphoramidates have the structure shown in FIG. 3. The inventive oligonucleotide structure shown in FIG. 3 was determined by first purifying and then analyzing the cleaved and deprotected reaction mixtures. The synthesized oligos were purified by ion exchange (IE) HPLC. The structure of the IE HPLC isolated oligo-2'-arabino-fluoronucleotide N3'→P5' phosphoramidates was confirmed by $^{31}$P and $^{19}$F NMR analysis.

The sequences of representative inventive oligonucleotides that have been prepared are summarized in Table 1.

TABLE 1

OLIGONUCLEOTIDES AND MELTING TEMPERATURE (Tm) VALUES OF THEIR COMPLEXES

| Expt. | 5'-Oligonucleotide-3'[a] | $T_m$, °C.[b] RNA | $T_m$, °C.[b] DNA | dsDNA[e] |
|---|---|---|---|---|
| 1 | d(UpUpUpUpUpUpUpUpT) [SEQ ID NO: 3] | 17.9;[c] 20.3[d] | 16.7;[c] 24.6[d] | n.o;[c] n.o[d] |
| 2 | r(Up$^f$Up$^f$Up$^f$Up$^f$Up$^f$Up$^f$Up$^f$Up$^f$Up$^f$T) [SEQ ID NO: 4] | 32.9; 36.6 | n.o; 18.0 | n.o; n.o |
| 3 | a(Up$^f$Up$^f$Up$^f$Up$^f$Up$^f$Up$^f$Up$^f$Up$^f$Up$^f$T) [SEQ ID NO: 5] | 27.5; 28.6 | 17.0; 25.0 | <14; 20.9 |
| 4 | d(UnUnUnUnUnUnUnUnUnT) [SEQ ID NO: 6] | 38.1; 47.2 | 18.5; 38.2 | <15; n.d |
| 5 | dT-r(Un$^f$Un$^f$Un$^f$Un$^f$Un$^f$Un$^f$Un$^f$Un$^f$Un$^f$) [SEQ ID NO: 7] | 55.5; 61.9 | 37.4; 56.3 | 42.2; 54.1 |
| 6 | dT-a(Un$^f$Un$^f$Un$^f$Un$^f$Un$^f$Un$^f$Un$^f$Un$^f$Un$^f$) [SEQ ID NO: 8] | 40.0; 40.0 | 25.7; 37.0 | 22.0; 31.2 |

TABLE 1-continued

OLIGONUCLEOTIDES AND MELTING TEMPERATURE (Tm)
VALUES OF THEIR COMPLEXES

| Expt. | 5'-Oligonucleotide-3'[a] | $T_m$, °C.[b] RNA | $T_m$, °C.[b] DNA | dsDNA[e] |
|---|---|---|---|---|
| 7 | d(CnUnCnUnCnUnGnCnCn) [SEQ ID NO: 9] | 66.7 | n.d | — |
| 8 | a(Cn$^f$Un$^f$Cn$^f$Un$^f$Cn$^f$Un$^f$GnCn$^f$Cn$^f$) [SEQ ID NO: 10] | 66.8 | n.d | — |

[a]d, r, and a correspond to the 2'-deoxy, 2'-ribo-fluoro and to 2'-arabino-fluorornucleosides respectively; p and n correspond to the internucleoside phosphodiester and N3'→P5' phosphoramidate linkages, respectively;
[b]melting temperature, $T_m$ (±0.5° C.), of the duplexes formed with natural phosphodiester ssDNA or RNA strands, or:
[e]triplexes formed with dA/dT duplex part of d(A$_{10}$C$_4$T$_{10}$) hairpin. Buffers:
[c]150 mM NaCl, 10 mM sodium phosphate buffer pH 7.4 - first number, or in:
[d]the same buffer containing an additional 10 mM magnesium chloride - second number; n.o or n.d - the melting transitions and $T_m$'s were not observed or not determined, respectively.

First, the compounds were characterized by ion exchange (IE) HPLC analysis. Oligo-2'-arabino-fluoronucleotide N3'→P5' phosphoramidate [SEQ ID NO:6], Table 1, has significantly longer, by about 8 minutes, retention time on IE HPLC column at pH 12, than that for the isosequential 2'-ribo-fluoro phosphoramidate counterpart oligonucleotide [SEQ ID NO:7], Table 1. At the same time these oligonucleotides practically co-elute from the same column at pH 7 buffer conditions. IE HPLC was carried out on Dionex DX 500 system, using Pharmacia MonoQ 5/5 column; Buffer A: 10 mM NaOH, pH12; Buffer B: 10 mM NaOH, 1.5 M NaCl, pH12; 1.5%/min. linear gradient of buffer B in A; flow 0.5 mL/min. Retention time (Rt), for co-injected oligonucleotides SEQ ID NOs:7, 8, 4 and 5, Table 1, was 33.6, 41.5, 42.5 and 46.5 minutes, respectively. At pH 7.2 (10 nM Na-phosphate buffer) retention times for oligonucleotides SEQ ID NOs:7 and 8 were 23.7 and 23.8 minutes, respectively. The different degrees of uracil base ionization under the alkaline conditions, as well as ionization of internucleoside 3'-NHP (O)O-5' groups, which are influenced by the spatial orientation of the 2'-fluorine likely determine the differences in the oligomers chromatographic behavior. Probably, the 2'-fluorine atom increases acidity of uracil bases and in trans-oriented internucleoside phosphoramidate groups better in ara-bino- than in ribo-configuration. Additionally, retention times (at pH 12) for the 2'-ribo-fluoro and 2'-arabino-fluoro phosphodiester decanucleotides SEQ ID NOs:4 and 5, Table 1, were noticeably longer, than for their phosphoramidate cognate oligonucleotides SEQ ID NOs:7 and 8, Table 1. This difference likely reflects a higher lypophilicity of 2'-fluoro phosphodiester oligonucleotides. Also, similarly to the phosphoramidates, oligo-2'-arabino-fluoronucleotide was retained longer than the 2'-ribo-fluoro isomer on IE HPLC column, indicating its higher net-negative charge in alkaline conditions.

Example 4

Stability and Duplex Formation Properties of N3'→P5' Phosphoramidate 2'-Arabino-Fluorooligonucleotides It was reported that the 2'-ribo-fluoropyrimidine containing oligonucleotides with N3'→P5' phosphoramidate or with phosphodiester internucleoside linkages are somewhat labile during treatment with aqueous ammonia at 55° C. (Schultz et al., *Nucl. Acids Res.*, 24:2966-2973, 1996; Krug et al., *Nucleosides Nucleotides*, 8:1473-1483, 1989). Under these basic conditions pyrimidine-O2 mediated elimination of the 2'-fluorine atom takes place, resulting in formation of 2,3'-O-anhydronucleosides and multiple products of their consequent reactions with aqueous ammonia, including 2'-arabino-hydroxyl nucleosides (Krug et al., *Nucleosides Nucleotides*, 8:1473-1483, 1989). In contrast, the prepared 2'-arabino-fluoro phosphoramidate oligonucleotides were stable under these conditions. The 2'-arabino-fluoro phosphoramidate decanucleotide SEQ ID NO:8, Table 1, was practically intact after exposure to concentrated aqueous ammonia for 24 hours, 55° C., whereas isomeric 2'-ribo-fluoro counterpart SEQ ID NO:7, Table 1, was converted into a very complex mixture of products under these conditions, as was judged by IE HPLC analysis. Moreover, the half-life of 2'-arabino-fluoro phosphoramidate SEQ ID NO:8 in acidic media, pH 3, was about 2 and 9 times longer (about 280 minutes), than that for the isosequential 2'-ribo-fluoro phosphoramidate oligonucleotide SEQ ID NO:7 (about 135 minutes) and for 2'-deoxy phosphoramidate oligonucleotide SEQ ID NO:6 (about 30 minutes), respectively (see Schultz, et al. 1996 for acid stability method).

The ability of N3'→P5' phosphoramidate 2'-arabino-fluorooligonucleotides to form complexes with complementary DNA and RNA strands was examined and compared with related oligonucleotide analogues using thermal denaturation experiments. The results of the study are summarized in Table 1. Substitution of 2'-deoxy nucleosides by their 2'-ribo-fluoro cognates in phosphodiester oligonucleotide, compounds SEQ ID NOs:3 and 4, resulted in significant stabilization of duplexes with RNA—$T_m$ of about 15.0-16.3° C., but destabilization of complexes with DNA—$T_m$ of about −6.7-16° C. (compare experiments 1 and 2, Table 1). 2'-arabino-fluoro and 2'-deoxy phosphodiester oligonucleotides SEQ ID NOs:5 and 10 formed duplexes of similar stability with DNA, but, with RNA the $T_m$ of the 2'-arabino-fluorooligonucleotide complex was about 8.3-9.6° C. higher than the 2'-deoxy phosphodiester oligonucleotide (compare experiments 1 and 3, Table 1). Substitution of 2'-deoxy-3'-aminonucleosides by 2'-arabino-fluoro-3'-amino counterparts stabilized duplexes, by about 2-7° C., with DNA and RNA in a low ionic strength buffer. In presence of an additional 10 mM magnesium chloride a 2'-deoxy phosphoramidate duplex with RNA is more stable, by about 7° C., than the duplex formed by a 2'-arabino-fluorooligonucleotide counterpart (compare experiments 4 and 6, Table 1). Interestingly, increasing the buffer ionic strength unexpectedly had no effect on $T_m$ value of oligonucleotide SEQ ID NO:6 duplex with RNA. Also, 2'-arabino-fluoro phosphoramidate SEQ ID NO:6 duplexes were more stable than those formed by a 2'-arabino-fluoro phosphodiester oligonucleotide SEQ ID NO:5, −$T_m$ 8.7-12.5° C. (compare experiments 3 and 6, Table 1). The most stable complexes with both DNA and RNA strands, $-T_m$ of about 14-21° C., were formed by 2'-ribo-fluoro phosphoramidate oligonucleotide SEQ ID NO:7 (compare experiments 5, 6 and 7, Table 1). Duplexes formed by the mixed base 2'-arabino-fluoro and 2'-deoxy phosphoramidate oligonucleotides SEQ ID NOs:9 and 10 have a similar thermal stability, which likely reflects similarity of the nucleosides sugar puckering, as indicated by the NMR analysis (compare experiments 7 and 8, Table 1). Moreover, 2'-arabino-fluoro phosphoramidate oligonucleotide SEQ ID NO:8 formed a more stable triplex with dsDNA than did a 2'-deoxy phosphoramidate oligonucleotide SEQ ID NO:6, or phosphodiester oligonucleotides SEQ ID NOs:3-5, but not a 2'-ribo-fluoro counterpart oligonucleotide SEQ ID NO:7 (Table 1). These data demonstrate the synergistic duplex and triplex stabilizing effects of 2'-arabino-fluoro and 3'-amino modifications.

Example 5

Preparation of Affinity Purified Extract Having Telomerase Activity

Extracts used for screening telomerase inhibitors were routinely prepared from 293 cells over-expressing the protein catalytic subunit of telomerase (hTERT). These cells were found to have 2-5 fold more telomerase activity than parental 293 cells. 200 ml of packed cells (harvested from about 100 liters of culture) were resuspended in an equal volume of hypotonic buffer (10 mM Hepes pH 7.9, 1 mM MgCl$_2$, 1 mM DTT, 20 mM KCl, 1 mM PMSF) and lysed using a dounce homogenizer. The glycerol concentration was adjusted to 10% and NaCl was slowly added to give a final concentration of 0.3 M. The lysed cells were stirred for 30 min. and then pelleted at 100,000×g for 1 hr. Solid ammonium sulfate was added to the S100 supernatant to reach 42% saturation. The material was centrifuged; the pellet was resuspended in one fifth of the original volume and dialyzed against Buffer 'A' containing 50 mM NaCl. After dialysis the extract was centrifuged for 30 min. at 25,000×g. Prior to affinity chromatography, Triton X-100 (0.5%), KCl (0.3 M) and tRNA (50 μg/ml) were added. Affinity oligo (5' biotinTEG-biotinTEG-biotinTEG-GTA GAC CTG TTA CCA guu agg guu ag 3' [SEQ ID NO:11]; lower case represents 2' O-methyl ribonucleotides and upper case represents deoxynucleotides) was added to the extract (1 mmol per 10 ml of extract). After an incubation of 10 min. at 30° C., Neutravidin beads (Pierce; 250 μl of a 50% suspension) were added and the mixture was rotated overnight at 4° C. The beads were pelleted and washed three times with Buffer 'B' containing 0.3 M KCl, twice with Buffer 'B' containing 0.6 M KCl, and twice more with Buffer B containing 0.3 M KCl. Telomerase was eluted in Buffer 'B' containing 0.3 M KCl, 0.15%. Triton X-100 and a 2.5 molar excess of displacement oligo (5'-CTA ACC CTA ACT GGT AAC AGG TCT AC-3' [SEQ ID NO:12] at 0.5 ml per 125 μl of packed Neutravidin beads) for 30 min. at room temperature. A second elution was performed and pooled with the first. Purified extracts typically had specific activities of 10 fmol nucleotides incorporated/min./μl extract, or 200 nucleotides/min./mg total protein.

| Buffer 'A' | Buffer 'B' |
|---|---|
| 20 mM Hepes pH 7.9 | 20 mM Hepes pH 7.9 |
| 1 mM MgCl2 | 1 mM EDTA |
| 1 mM DTT | 1 mM DTT |
| 1 mM EGTA | 10% glycerol |
| 10% glycerol | 0.5% Triton X-100 |

Example 6

Telomerase Inhibition by Oligonucleotide N3'→P5' 2'-Arabino-Fluoro Phosphoramidates Three separate 100 μl telomerase assays are set up with the following buffer solutions: 50 mM Tris acetate, pH 8.2, 1 mM DTT, 1 mM EGTA, 1 mM MgCl$_2$, 100 mM K acetate, 500 μM dATP, 500 μM TTP, 10 μM $^{32}$P-dGTP (25 Ci/mmol), and 100 nM d(TTAGGG)$_3$ [SEQ ID NO: 13]. To the individual reactions 2.5, 5 or 10 μl of affinity-purified telomerase (see Example 5) is added and the reactions are incubated at 37 C. At 45 and 90 minutes, 40 μl aliquots are removed from each reaction and added to 160 μl of Stop Buffer (100 mM NaCl, 10 mM Na pyrophosphate, 0.2% SDS, 2 mM EDTA, 100 μg/ml tRNA). 10 μl trichloroacetic acid (TCA) (100%) is added and the sample is incubated on ice for 30 minutes. The sample is pelleted in a microcentrifuge (12000×g force) for 15 minutes. The pellet is washed with 1 ml 95% ethanol and pelleted again in the microcentrifuge (12000×g force) for 5 minutes. The pellet is resuspended in 50 μl dH$_2$O and transferred to a 12×75 glass test tube containing 2.5 ml of ice cold solution of 5% TCA and 10 mM Na pyrophosphate. The sample is incubated on ice for 30 minutes. The sample is filtered through a 2.5 cm wet (dH$_2$O) GFC membrane (S&S) on a vacuum filtration manifold. The filter is washed three times under vacuum with 5 ml ice cold 1% TCA, and once with 5 ml 95% ethanol. The filter is dried and counted in a scintillation counter using scintillation fluid. The fmol of nucleotide incorporated is determined from the specific activity of radioactive tracer. The activity of extract is calculated based on the dNTP incorporated and is expressed as fmol dNTP/min./μl extract.

Telomerase Activity Assay

Bio-Tel FlashPlate Assay

An assay is provided for the detection and/or measurement of telomerase activity by measuring the addition of TTAGGG telomeric repeats to a biotinylated telomerase substrate primer; a reaction catalyzed by telomerase. The biotinylated products are captured in streptavidin-coated microtiter plates. An oligonucleotide probe complementary to 3.5 telomere repeats labeled with [$^{33}$P] is used for measuring telomerase products, as described below. Unbound probe is removed by washing and the amount of probe annealing to the captured telomerase products is determined by scintillation counting.
Method:
I. 2'-Arabino-fluoro phosphoramidate oligonucleotides were stored as concentrated stocks and dissolved in PBS.
II. For testing, the 2'-arabino-fluoro phosphoramidate oligonucleotides were diluted to a 15× working stock in PBS and 2 μl was dispensed into two wells of a 96-well microtiter dish (assayed in duplicate).
III. Telomerase extract was diluted to a specific activity of 0.04-0.09 fmol dNTP incorporated/min./μl in Telomerase Dilution Buffer and 18 Pl added to each sample well to preincubate with compound for 30 minutes at room temperature.

IV. The telomerase reaction was initiated by addition of 10 μl Master Mix to the wells containing telomerase extract and oligonucleotide compound being tested. The plates were sealed and incubated at 37° C. for 90 min.

V. The reaction was stopped by the addition of 10 μl HCS.

VI. 25 μl of the reaction mixture was transferred to a 96-well streptavidin-coated FlashPlate (NEN) and incubated for 2 hours at room temperature with mild agitation.

VII. The wells were washed three times with 180 μl 2×SSC without any incubation.

VIII. The amount of probe annealed to biotinylated telomerase products were detected in a scintillation counter.

IX.

Buffers:
Telomerase Dilution Buffer
  50 mM Tris-acetate, pH 8.2
  1 mM DTT
  1 mM EGTA
  1 mM $MgCl_2$
  830 nM BSA
Master Mix (MM)
  50 mM Tris-acetate, pH 8.2
  1 mM DTT
  1 mM EGTA
  1 mM $MgCl_2$
  150 mM K acetate
  10 μM dATP
  20 μM dGTP
  120 μM dTTP
  100 nM biotinylated primer (5'-biotin-AATCCGTCGAG-CAGAGTT-3') [SEQ ID NO:14]
  5.4 nM labeled probe [5'-CCCTAACCCTAAC-CCTAACCC-($^{33}$P)$A_{1\text{-}50}$-3'][SEQ ID NO:15]; specific activity approximately $10^9$ cpm/μg or higher
Hybridization Capture Solution (HCS)
  12×SSC (1×=150 mM NaCl/30 mM $Na_3$Citrate)
  40 mM EDTA
  40 mM Tris-HCl, pH 7.0

Using the foregoing assay, $IC_{50}$ values for the inventive 2'-arabino-fluoro phosphoramidate oligonucleotides represented by the sequences shown in Table 2 can be determined.

TABLE 2

| 2'-ARABINO-FLUOROOLIGONUCLEOTIDES 1-4 AS TELOMERASE INHIBITORS IN COMPARISON WITH 2'-RIBOSE-FLUORO PHOSPHORAMIDATES: |
| --- |
| SEQ ID NOs  5'-Oligonucleotide-3'$^a$ |
| SEQ ID NO: 16 dG-a (Tn/Tn/An/Gn/Gn/Gn/Tn/Tn/An/Gn/) |
| SEQ ID NO: 17 dG-a (Tn/Tn/Gn/An/Gn/Tn/Gn/Tn/An/Gn/) |
| SEQ ID NO: 18 dT-a (An/Gn/Gn/Gn/Tn/Tn/An/Gn/An/Cn/An/An/) |
| SEQ ID NO: 19 dT-a (An/Gn/Gn/Tn/Gn/Tn/An/An/Gn/Cn/An/An/) |
| SEQ ID NO: 20 dG-r (Tn/Tn/An/Gn/Gn/Gn/Tn/Tn/An/Gn/) |
| SEQ ID NO: 21 dG-r (Tn/Tn/Gn/An/Gn/Tn/Gn/Tn/An/Gn$^p$) |
| SEQ ID NO: 22 dT-r (An/Gn/Gn/Gn/Tn/Tn/An/Gn/An/Cn/An/An/) |

TABLE 2-continued

| 2'-ARABINO-FLUOROOLIGONUCLEOTIDES 1-4 AS TELOMERASE INHIBITORS IN COMPARISON WITH 2'-RIBOSE-FLUORO PHOSPHORAMIDATES: |
| --- |
| SEQ ID NOs  5'-Oligonucleotide-3'$^a$ |
| SEQ ID NO: 23 dT-r (An/Gn/Gn/Tn/Gn/Tn/An/An/Gn/Cn/An/An/) |

$^a$d, r, and a correspond to the 2'deoxy, 2'ribo-fluoro and to 2'-arabino-fluorornucleosides respecitvely; p and n correspond to the internucleoside phosphodiester and N3'→P5'phosphoramidate linkages, respecitvely.

Oligonucleotides SEQ ID NOs:17 and 19 are mismatch controls for oligonucleotides SEQ ID NOs:16 and 18, respectively, that are used to compare the telomerase inhibiting power of 2'-arabino-fluoro phosphoramidate oligonucleotides to corresponding 2'-ribose-fluoro phoshoramidate analog oligonucleotides. Similarly, oligonucleotides SEQ ID NOs:21 and 23 are mismatch controls for the oligonucleotides SEQ ID NOs:20 and 22.

Based upon the thermal stability of the inventive oligonucleotides (Table 1), it is anticipated that a telomerase inhibition assay performed using 2'-arabino-fluoro phosphoramidate polynucleotides SEQ ID NOs:16 and 18 of Table 2 will be more effective at inhibiting telomerase activity than their counterpart 2'-ribose-fluorooligonucleotides SEQ ID NO:20 and 22. Thus, the 2'-arabino-fluoro phosphoramidate oligonucleotides of the present invention are expected to be not only more active in the telomerase inhibition assay as compared to their 2'-ribose-fluorooligonucleotides counterparts, but are also more acid resistant than them as well (see Table 1). This combination of characteristics imparts the inventive 2'-arabino-fluoro phosphoramidate oligonucleotides with an important advantage compared to 2'-ribose-fluoro phosphoramidate polynucleotides.

Example 7

Anti-Tumor Activity of 2'-Arabino-Fluoro Phosphoramidate Oligonucleotides

Ex Vivo Studies a. Reduction of Telomere Length in Tumor Cells

Colonies of the tumor cell lines, such as the ovarian tumor cell lines OVCAR-5, and SK-OV-3, and normal human cells used as a control (e.g., normal human BJ cells) are prepared using standard methods and materials. In one test, the colonies are prepared by seeding 15-centimeter dishes with about $10^6$ cells in each dish. The dishes are incubated to allow the cell colonies to grow to about 80% confluence, at which time each of the colonies are divided into two groups. One group is exposed to a subacute dose of a 2'-arabino-fluoro phosphoramidate oligonucleotide of the invention at a predetermined concentration (e.g., between about 100 nM and about 20 μM) for a period of about 4-8 hours after plating following the split; the other group is exposed to a control (e.g., a phosphoramidate oligonucleotide complementary to telomerase RNA but having at least one base sequence that is mismatched relative to the sequence of telomerase RNA.

Each group is then allowed to continue to divide, and the groups are split evenly again (near confluence). The same number of cells are seeded for continued growth. The test 2'-arabino-fluoro phosphoramidate oligonucleotide or control oligonucleotide is added every fourth day to the samples at the same concentration delivered initially. Remaining cells are analyzed for telomere length. As the untested cell cultures near confluence, the samples are split again as just described.

This sequence of cell doubling and splitting is continued for about 20 to 25 doublings. Thus, a determination of telomere length as a function of cell doublings is obtained.

Telomere length is determined by digesting the DNA of the cells using restriction enzymes specific for sequences other than the repetitive $T_2 AG_3$ sequence of human telomeres (TRF analysis). The digested DNA is separated by size using standard techniques of gel electrophoresis to determine the lengths of the telomeric repeats, which appear, after probing with a telomere DNA probe, on the gel as a smear of high-molecular weight DNA (approximately 2 Kb-15 Kb).

The results of the telomere length analysis are expected to indicate that the 2'-arabino-fluoro phosphoramidate oligonucleotides of the invention have no affect on the rate of decrease in telomere length for control cells as a function of progressive cell doublings. With respect to the tumor cell lines, however, measurable decreases in telomere length are expected to be determined for tumor cells exposed to the 2'-arabino-fluoro phosphoramidate oligonucleotides of the invention. Tumor cells exposed to the control oligonucleotides are expected to maintain steady telomere lengths. Thus, the compounds of the invention are expected to cause resumption of the normal loss of telomere length as a function of cell division in tumor cells.

In another experiment, HEK-293 cells are incubated with a 2'-arabino-fluoro phosphoramidate oligonucleotide of the invention and a control oligonucleotide at concentrations between about 0.1 µM and about 20 µM using the protocol just described. Cells are expected to enter crisis (i.e., the cessation of cell function) within several weeks following administration of the test 2'-arabino-fluoro phosphoramidate oligonucleotides of the invention. In addition, TRF analysis of the cells using standard methodology is expected to show that the test 2'-arabino-fluoro phosphoramidate oligonucleotides of the invention are effective in reducing telomere length. In addition to the HEK-293 cells described above, this assay can be performed with any telomerase-positive cell line, such as HeLa cells.

b. Specificity

Phosphoramidate 2'-arabino-fluoro oligonucleotides of the invention are screened for activity ($IC_{50}$) against telomerase and other enzymes known to have RNA components by performing hybridization tests or enzyme inhibition assays using standard techniques. Oligonucleotides having lower $IC_{50}$ values for telomerase as compared to the $IC_{50}$ values toward the other enzymes being screened are said to possess specificity for telomerase.

c. Cytotoxicity

The XTT assay for cytotoxicity is performed using HeLa cells. The cell lines used in the assay are exposed to a 2'-arabino-fluoro phosphoramidate oligonucleotide of the invention for 72 hours at concentrations ranging from about 1 µM to about 100 µM. During this period, the optical density (OD) of the samples is determined for light at 540 nanometers (nm).

No significant cytotoxic effects are expected to be observed at concentrations less than about 20 µM. It will be appreciated that other tumor cells lines such as the ovarian tumor cell lines OVCAR-5 and SK-OV-3 can be used to determine cytotoxicity in addition to control cell lines such as normal human BJ cells. Other assays for cytotoxicity such as the MTT assay (see Berridge et al., *Biochemica* 4:14-19, 1996) and the alamarBlue™ assay (U.S. Pat. No. 5,501,959) can be used as well.

Preferably, to observe any telomerase inhibiting effects the 2'-arabino-fluoro phosphoramidate oligonucleotides should be administered at a concentration below the level of cytotoxicity. Nevertheless, since the effectiveness of many cancer chemotherapeutics derives from their cytotoxic effects, it is within the scope of the present invention that the phosphoramidate oligonucleotides of the present invention be administered at any dose for which chemotherapeutic effects are observed.

In Vivo Studies

A human tumor xenograft model in which OVCAR-5 tumor cells are grafted into nude mice can be constructed using standard techniques and materials. The mice are divided into two groups. One group is treated intraperitoneally with a 2'-arabino-fluoro phosphoramidate oligonucleotides of the invention. The other group is treated with a control comprising a mixture of phosphate buffer solution (PBS) and an oligonucleotide complementary with telomerase RNA but has at least a one base mismatch with the sequence of telomerase RNA. The average tumor mass for mice in each group is determined periodically following the xenograft using standard methods and materials.

In the group treated with a 2'-arabino-fluoro phosphoramidate oligonucleotide of the invention, the average tumor mass is expected to increase following the initial treatment for a period of time, after which time the tumor mass is expected to stabilize and then begin to decline. Tumor masses in the control group are expected to increase throughout the study. Thus, the 2'-arabino-fluoro phosphoramidate oligonucleotides of the invention are expected to lessen dramatically the rate of tumor growth and ultimately induce reduction in tumor size and elimination of the tumor.

Thus, the present invention provides novel 2'-arabino-fluoro phosphoramidate oligonucleotides and methods for inhibiting telomerase activity and treating disease states in which telomerase activity has deleterious effects, especially cancer. The phosphoramidate 2'-arabino-fluoro oligonucleotides of the invention provide a highly selective and effective treatment for malignant cells that require telomerase activity to remain immortal; yet, without affecting non-malignant cells.

While the preferred embodiment of the invention has been illustrated and described, it will be appreciated that various changes can be made therein without departing from the spirit and scope of the invention.

The invention claimed is:

1. A compound of the formula:

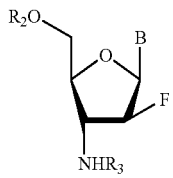

wherein:
B is a purine or pyrimidine or a base analog thereof;
$R_2$ is lower alkyl, $PO_3$, or $PN(R_4)_2OR_5$ wherein $R_4$ is alkyl, and $R_5$ is cyano-lower alkyl; and
$R_3$ is hydrogen or substituted or unsubstituted trityl.

2. A compound according to claim 1, wherein $R_2$ is $PN(R_4)_2OR_5$ wherein $R_4$ is isopropyl, $R_5$ is β-cyanoethyl and $R_3$ is monomethoxytrityl.

3. A compound according to claim 1, wherein the constituent B is exocyclic amino protected.

4. A compound according to claim 1, wherein B is $N_2$-isobutyrylguanine, B is 2,6-diaminopurine and the exocyclic amine groups of 2,6-diaminopurine are protected with a phenoxyacetyl group, or B is cytosine and the N4 amino group of cytosine is protected with a benzoyl group.

5. A compound of the formula:

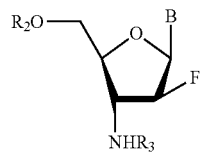

wherein:
B is a purine or pyrimidine or a base analog thereof;
$R_2$ is $PN(R_4)_2OR_5$ wherein $R_4$ is isopropyl, and $R_5$ is β-cyanoethyl; and
$R_3$ is hydrogen or substituted or unsubstituted trityl.

* * * * *